(12) United States Patent
Hansen et al.

(10) Patent No.: US 11,241,576 B2
(45) Date of Patent: Feb. 8, 2022

(54) CONTROLLED POSITION ELECTRODE ARRAY

(71) Applicant: UNIVERSITY OF IOWA RESEARCH FOUNDATION, Iowa City, IA (US)

(72) Inventors: Marlan R. Hansen, Solon, IA (US); Christopher Kaufmann, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 633 days.

(21) Appl. No.: 15/759,643

(22) PCT Filed: Jun. 24, 2016

(86) PCT No.: PCT/US2016/039342
§ 371 (c)(1),
(2) Date: Mar. 13, 2018

(87) PCT Pub. No.: WO2017/048342
PCT Pub. Date: Mar. 23, 2017

(65) Prior Publication Data
US 2019/0282803 A1    Sep. 19, 2019

Related U.S. Application Data

(60) Provisional application No. 62/218,359, filed on Sep. 14, 2015.

(51) Int. Cl.
*A61N 1/05* (2006.01)
*A61N 1/36* (2006.01)
(Continued)

(52) U.S. Cl.
CPC ........ *A61N 1/0541* (2013.01); *A61B 17/3468* (2013.01); *A61N 1/36038* (2017.08); *H01L 41/09* (2013.01); *H04B 5/0037* (2013.01)

(58) Field of Classification Search
CPC .............. A61N 1/0541; A61N 1/36038; A61B 17/3468
See application file for complete search history.

(56) References Cited

U.S. PATENT DOCUMENTS 3,610,877 A   10/1971   Driscoll
4,383,532 A    5/1983   Dickhudt
(Continued)

FOREIGN PATENT DOCUMENTS

CA    2997735 A1     3/2017
CN   110430918 A    11/2019
(Continued)

OTHER PUBLICATIONS

International Search Report and Written Opinion corresponding to International Patent Application No. PCT/US2016/039342, dated Oct. 6, 2016.
(Continued)

*Primary Examiner* — Mallika D Fairchild
*Assistant Examiner* — Vynn V Huh
(74) *Attorney, Agent, or Firm* — Schwegman Lundberg & Woessner, P.A.

(57) ABSTRACT

The present embodiment is an implantable device capable of controlling cochlear implant electrode insertion and positioning. The embodiment uses an implanted mechanical positioning unit to advance position and monitor an electrode array. The device can be controlled via an external controller to reposition or advance an electrode array at any point after implantation with no surgical re-intervention. A cochlear implant electrode array whose position can be advanced and modified over time to best fit a patient's evolving hearing pattern would improve functional out-
(Continued)

comes and significantly expand the candidacy range for cochlear implantation to include patients with substantial residual hearing.

21 Claims, 15 Drawing Sheets

(51) Int. Cl.
*A61B 17/34* (2006.01)
*H01L 41/09* (2006.01)
*H04B 5/00* (2006.01)

(56) References Cited

U.S. PATENT DOCUMENTS

| | | |
|---|---|---|
| 4,532,930 A | 8/1985 | Crosby et al. |
| 4,637,404 A | 1/1987 | Gessman |
| 5,201,765 A | 4/1993 | Netterville et al. |
| 5,306,298 A | 4/1994 | Godley, III et al. |
| 5,593,439 A | 1/1997 | Cummings et al. |
| 5,758,396 A | 6/1998 | Jeon et al. |
| 7,524,320 B2 | 4/2009 | Tierney et al. |
| 7,691,098 B2 | 4/2010 | Wallace et al. |
| 8,010,210 B2 | 8/2011 | Rau |
| 8,229,574 B2 | 7/2012 | Parker et al. |
| 8,583,261 B2 | 11/2013 | Llinas et al. |
| 8,594,799 B2 | 11/2013 | Haller et al. |
| 8,886,331 B2 | 11/2014 | Labadie et al. |
| 9,675,446 B2 | 6/2017 | Jaber et al. |
| 9,700,408 B1 | 7/2017 | Sataloff |
| 9,986,998 B2 | 6/2018 | Martin et al. |
| 10,085,806 B2 | 10/2018 | Hagn et al. |
| 10,945,761 B2 | 3/2021 | Kaufmann et al. |
| 2003/0171758 A1 | 9/2003 | Gibson et al. |
| 2004/0236390 A1 | 11/2004 | Dadd et al. |
| 2005/0004627 A1 | 1/2005 | Gibson et al. |
| 2005/0245991 A1 | 11/2005 | Faltys et al. |
| 2006/0241723 A1 | 10/2006 | Dadd et al. |
| 2007/0156123 A1 | 7/2007 | Moll et al. |
| 2007/0225787 A1 | 9/2007 | Simaan et al. |
| 2008/0077221 A1 | 3/2008 | Milojevic et al. |
| 2008/0188931 A1 | 8/2008 | Kwon |
| 2010/0114288 A1* | 5/2010 | Haller ............... A61B 34/30 607/137 |
| 2010/0145138 A1* | 6/2010 | Forsell ............... A61F 2/0036 600/30 |
| 2010/0145143 A1 | 6/2010 | Salomon et al. |
| 2011/0106101 A1* | 5/2011 | Tortonese ......... A61M 25/0147 606/129 |
| 2011/0208031 A1* | 8/2011 | Wolfe ............... A61B 5/291 600/378 |
| 2011/0264038 A1 | 10/2011 | Fujimoto et al. |
| 2012/0041531 A1 | 2/2012 | Dadd et al. |
| 2012/0071890 A1 | 3/2012 | Taylor et al. |
| 2012/0150293 A1 | 6/2012 | Hoffman et al. |
| 2013/0138117 A1 | 5/2013 | Abbott et al. |
| 2013/0172901 A1 | 7/2013 | Bozorg et al. |
| 2013/0245569 A1 | 9/2013 | Jolly et al. |
| 2013/0296884 A1 | 11/2013 | Taylor et al. |
| 2013/0331779 A1 | 12/2013 | Dhanasingh et al. |
| 2014/0222207 A1 | 8/2014 | Bowling et al. |
| 2014/0276391 A1 | 9/2014 | Yu |
| 2014/0350640 A1 | 11/2014 | Patrick et al. |
| 2014/0358174 A1 | 12/2014 | Thenuwara et al. |
| 2015/0032123 A1 | 1/2015 | Jolly et al. |
| 2015/0032124 A1 | 1/2015 | Lenarz et al. |
| 2015/0105795 A1 | 4/2015 | Lenarz et al. |
| 2015/0342445 A1 | 12/2015 | Jones et al. |
| 2016/0038733 A1* | 2/2016 | Robinson ............... A61N 1/18 607/116 |
| 2016/0056493 A1 | 2/2016 | Umeda et al. |
| 2018/0021568 A1 | 1/2018 | Schachteie et al. |
| 2018/0242967 A1 | 8/2018 | Meade |
| 2019/0029668 A1 | 1/2019 | Meade et al. |
| 2019/0142247 A1 | 5/2019 | Maeda et al. |
| 2020/0038106 A1 | 2/2020 | Pieper et al. |
| 2020/0046978 A1 | 2/2020 | Kaufmann et al. |
| 2020/0069386 A1 | 3/2020 | Betsugi et al. |
| 2020/0329950 A1 | 10/2020 | Shear et al. |
| 2020/0337725 A1 | 10/2020 | Kaufmann et al. |
| 2021/0187294 A1 | 6/2021 | Kaufmann et al. |
| 2021/0187295 A1 | 6/2021 | Kaufmann et al. |

FOREIGN PATENT DOCUMENTS

| | | |
|---|---|---|
| CN | 112074254 A | 12/2020 |
| EP | 2113283 A1 | 11/2009 |
| EP | 3334492 A1 | 6/2018 |
| EP | 3334492 B1 | 6/2019 |
| EP | 3662971 A1 | 6/2020 |
| WO | WO-2017048342 A1 | 3/2017 |
| WO | WO-2017177208 A1 | 10/2017 |
| WO | WO-2018152203 A2 | 8/2018 |
| WO | WO2018152203 A3 | 10/2018 |
| WO | WO-2019173107 A1 | 9/2019 |

OTHER PUBLICATIONS

International Bureau, "Preliminary Report on Patentability," issued in connection with International Patent Application No. PCT/US2016/039342, dated Mar. 29, 2018, 9 pages.
"Australian Application Serial No. 2016323477, First Examination Report dated Jun. 29, 2020", 3 pgs.
"European Application Serial No. 16736687.1, Intention to Grant dated Jan. 7, 2019", 48 pgs.
"European Application Serial No. 19173377.3, Extended European Search Report dated Mar. 4, 2020", 4 pgs.
"European Application Serial No. 19173377.3, Response filed Oct. 25, 2020 to Extended European Search Report dated Mar. 4, 2020", 22 pgs.
"International Application Serial No. PCT/US2016/039342, International Search Report dated Oct. 6, 2016", 4 pgs.
"International Application Serial No. PCT/US2016/039342, Written Opinion dated Oct. 6, 2016", 7 pgs.
U.S. Appl. No. 17/196,690, filed Mar. 9, 2021, Modular Implant Delivery and Positioning System.
U.S. Appl. No. 17/196,723, filed Mar. 9, 2021, Modular Implant Delivery and Positioning System.
"U.S. Appl. No. 16/486,030, Corrected Notice of Allowability dated Jan. 12, 2021", 7 pgs.
"U.S. Appl. No. 16/486,030, Non Final Office Action dated Sep. 8, 2020", 12 pgs.
"U.S. Appl. No. 16/486,030, Notice of Allowance dated Dec. 24, 2020", 11 pgs.
"U.S. Appl. No. 16/486,030, Preliminary Amendment Filed Aug. 14, 2019", 10 pgs.
"U.S. Appl. No. 16/486,030, Response filed Aug. 10, 2020 to Restriction Requirement dated Jun. 11, 2020", 8 pgs.
"U.S. Appl. No. 16/486,030, Response filed Dec. 8, 2020 to Non Final Office Action dated Sep. 8, 2020", 12 pgs.
"U.S. Appl. No. 16/486,030, Restriction Requirement dated Jun. 11, 2020", 7 pgs.
"U.S. Appl. No. 16/486,030, Supplemental Preliminary Amendment filed", 8 pgs.
"U.S. Appl. No. 16/926,335, Notice of Allowance dated Nov. 9, 2020", 14 pgs.
"U.S. Appl. No. 16/926,335, Response filed Oct. 2, 2020 to Restriction Requirement dated Aug. 4, 2020", 9 pgs.
"U.S. Appl. No. 16/926,335, Restriction Requirement dated Aug. 4, 2020".
"U.S. Appl. No. 16/979,427 Preliminary Amendment filed Sep. 9, 2020", 10 pgs.
"U.S. Appl. No. 17/196,723, Corrected Notice of Allowability dated Jul. 7, 2021", 2 pgs.
"U.S. Appl. No. 17/196,723, Notice of Allowance dated Jun. 23, 2021", 8 pgs.

(56) References Cited

OTHER PUBLICATIONS

"Australian Application Serial No. 2016323477, Response filed Dec. 10, 2020 to First Examination Report dated Jun. 29, 2020", 19 pgs.
"Australian Application Serial No. 2019231573, First Examination Report dated Feb. 8, 2021", 6 pgs.
"Chinese Application Serial No. 201880011446.0, Voluntary Amendment filed Feb. 28, 2020", w/English claims, 7 pgs.
"European Application Serial No. 18707575.9, Response to Communication Pursuant to Rules 161 and 162 filed Feb. 25, 2020", 23 pgs.
"International Application Serial No. PCT/US2018/018182, International Preliminary Report on Patentability dated Aug. 29, 2019", 14 pgs.
"International Application Serial No. PCT/US2018/018182, International Search Report dated Sep. 10, 2018", 7 pgs.
"International Application Serial No. PCT/US2018/018182, Invitation to Pay Add'l Fees and Partial Search Report dated May 23, 2018", 15 pgs.
"International Application Serial No. PCT/US2018/018182, Written Opinion dated Sep. 10, 2018", 12 pgs.
"International Application Serial No. PCT/US2019/020130, International Preliminary Report on Patentability dated Sep. 24, 2020", 7 pgs.
"International Application Serial No. PCT/US2019/020130, International Search Report dated Jun. 12, 2019", 7 pgs.
"International Application Serial No. PCT/US2019/020130, Written Opinion dated Jun. 12, 2019", 10 pgs.
Campbell, Luke, et al., "Intraoperative Real-time Cochlear Response Telemetry Predicts Hearing Preservation in Cochlear Implantation", Otology & Neurotology; vol. 37(4), (Apr. 2016), 10 pgs.
Dahm, MC, et al., "The postnatal growth of the temporal bone and its implications for cochlear implantation in children", Acta Otolaryngol Suppl. 505., (1993), 4-39.
Desrosiers, M, et al., "Precise vocal cord medialization using an adjustable laryngeal implant: a preliminary study", Otolaryngol Head Neck Sur, 109(6), (1993), 1014-1019.
Gantz, Bruce J., et al., "Hybrid 10 Clinical Trial", Audiol Neurotol 2009;14(suppl 1): DOI: 10.1159/000206493, (2009), 7 pgs.
Greene, Nathaniel, et al., "Intracochlear pressure transients during cochlear implant electrode insertion", Otol Neurotol. 37(10), (2016), 1541-1548.
Jurawitz, Marie-Charlot, et al., "Hearing Preservation Outcomes with Different Cochlear Implant Electrodes: Nucleus® Hybrid TM-L24 and Nucleus Freedom TM CI422", Audiol Neurotol 2014;19: 293-309; DOI: 10.1159/000360601, (2014), 17 pgs.
Mittmann, Phillipp, et al., "Intracochlear Pressure Changes due to 2 Electrode Types: An Artificial Model Experiment", Otolaryngoloqy—Head and Neck Surgery, vol. 156(4), (Dec. 2016), 712-716.
Montgomery, William, et al., "Montgomery Thyroplasty Implant for vocal fold immobility: phonatory outcomes", Ann Otol Rhinol Laryngol, 109(4), (2000), 393-400.
Mowry, Sarah E., et al., "New Frontiers in Cochlear Implantation: Acoustic Plus Electric Hearing, Hearing Preservation, and More", Otolaryngologic Clinics of North America. vol. 45, Issue 1., (2012), 187-203.
Woodson, Erika A., et al., "The Hybrid Cochlear Implant: A Review", Cochlear Implants and Hearing Preservation. Adv Otorhinolaryngol. Basel, Karger, 2010, vol. 67., (2010), 125-134.
"Canadian Application Serial No. 2997735, Response filed Sep. 20, 2021 to Office Action dated Jun. 17, 2021", 62 pgs.

\* cited by examiner

Hybrid L24

FREQUENCIES THAT ARE AUDIBLE:

The cochlea function when stimulated with the Hybrid System

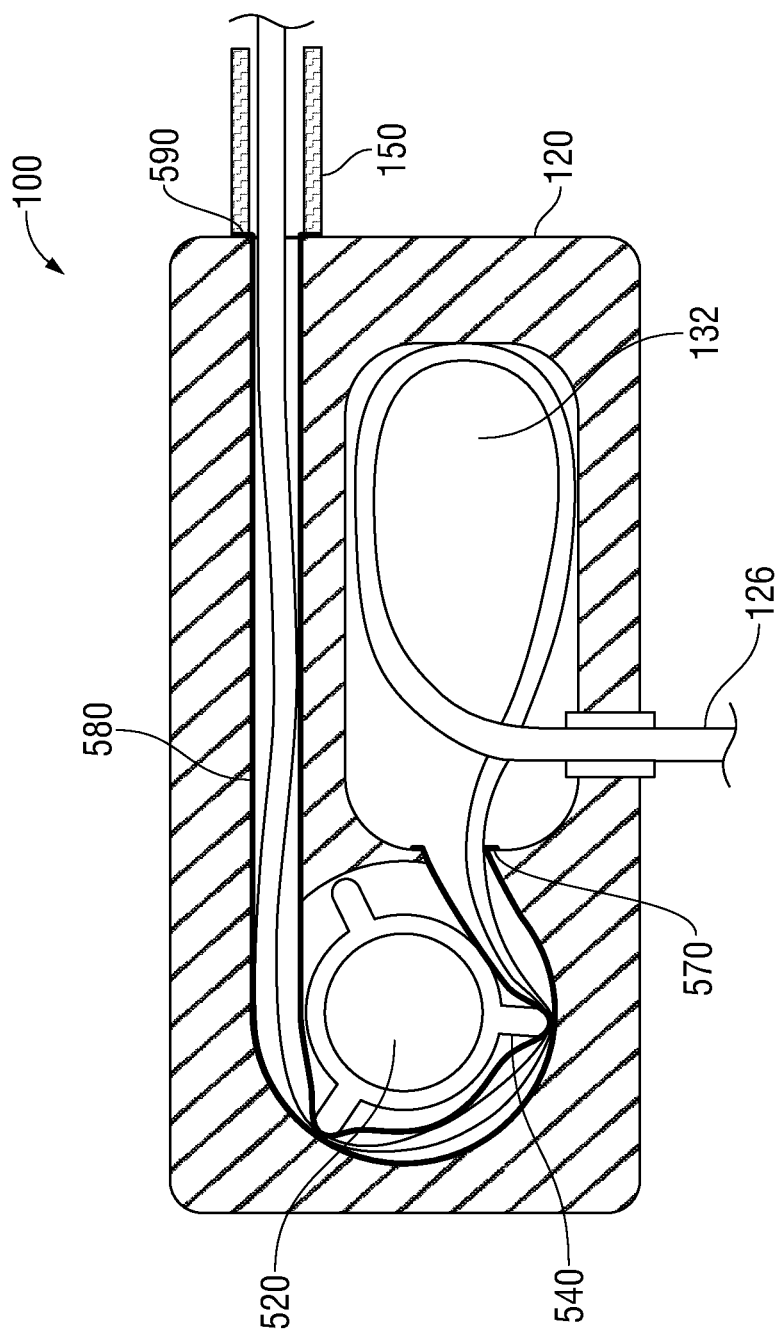

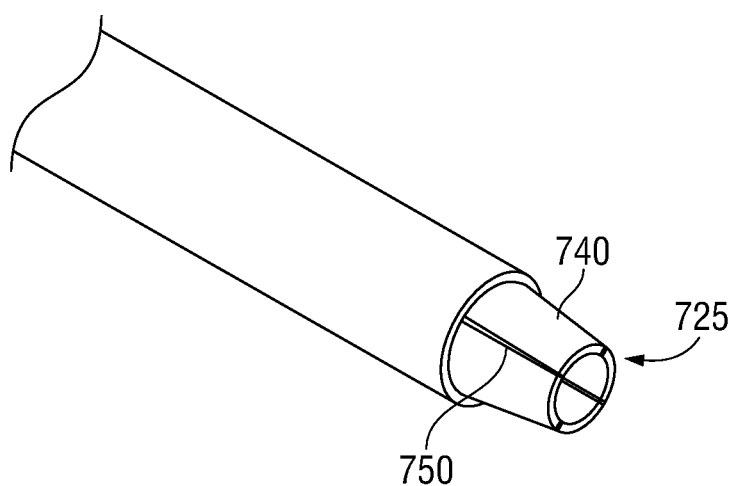
FIG. 8a
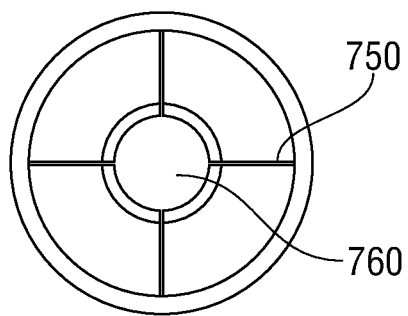 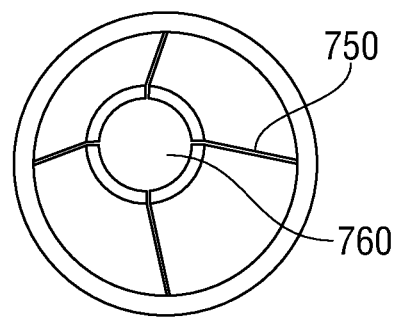
FIG. 8b  FIG. 8c

CONTROLLED POSITION ELECTRODE ARRAY

RELATED APPLICATION

This application is a national phase filing and claims priority of International Patent Application No. PCT/US2016/039342, having an International filing date of Jun. 24, 2016, which claims priority to U.S. provisional patent application Ser. No. 62/218,359, filed Sep. 14, 2015. The entire contents of the provisional application and international patent application referred to above is incorporated by reference.

FEDERALLY SPONSORED RESEARCH OR DEVELOPMENT

This work was made with government support under grant in part by NIH grant NIDCD 5T32DC000040. The government has certain rights in the invention.

FIELD OF THE INVENTION

The present embodiment relates to medical or biotechnological hearing restoration or neural prosthesis, and to an apparatus and a method related to a controlled position electrode array.

BACKGROUND

There are 360 million people worldwide—5% of the global population—with moderate to profound hearing loss (>40 db). Hearing loss has a significant impact on children and adults' physical and mental health, education, employment, and overall quality of life. Severe to profound hearing loss affects an estimated 53 million people worldwide. An additional 300 million people have disabling moderate to severe hearing loss which may be due to partial damage to the cochlea in the high frequency regions from common causes such as noise exposure, drugs, genetic mutations or aging. These individuals maintain "good" low frequency hearing, yet do not significantly benefit from hearing aids and are not eligible for a traditional full length electrode due to the risk of damage to their "good" residual hearing.

Cochlear implants have significantly impacted the treatment of severe hearing loss over the last 30 years. Next generation implant technologies preserve residual good hearing to enable improved performance. The recently FDA-approved Hybrid cochlear implant utilizes a short electrode for electrical stimulation of high frequency ranges combined with conventional acoustic hearing for the low frequency ranges in the same ear. This "electrical acoustic stimulation" (EAS) has dramatically improved hearing outcomes, specifically in difficult listening situations such as speech recognition in noisy environments or music appreciation. It has expanded the cochlear implant candidacy range to those who previously could not receive one including patients with high-frequency hearing losses who have normal or near normal pre-operative hearing in the low frequency ranges.

Referring to FIG. 1a, the cochlea is the portion of the inner ear dedicated to hearing. It comprises a spiraled, hollow, conical chamber of bone in which sound waves propagate from the base to the apex. This vibrates a liquid (perilymph) that moves hairs in the organ of Corti, converting the vibrations to electrical signals sent to the cochlear nerve. As shown in FIG. 1b, the cochlea has a "snail shell" appearance where the spiral tightens farther into the cochlea that sound waves progress. The hair cells and nerves in the basal, the outer, first part of the spiral, are more sensitive to higher frequencies and are frequently the first part of the cochlea to lose sensitivity. Lower frequencies are found deeper into the spiral and many people suffering hearing loss retain some hearing in this part of the cochlea. For patients who have residual, low frequency hearing, a shorter electrode implant for stimulation may be indicated.

FIG. 2 shows a typical cochlear implant arrangement. A cochlear implant is an implanted surgical device comprising an external sound processor and transmitter that converts sound into electrical signals then transmits the signal to a receiver implanted under the skin. The receiver converts the signal to electrical impulses sent down an electrode to an array of contacts. The electrode assembly is surgically inserted into the cochlea. The array is electrically stimulated based on the frequencies received, with higher frequencies resulting in stimulation in the "basal" region and lower frequencies stimulating the cochlea farther into the distal end of the spiral or the "apical" region. For patients who have good residual, low frequency hearing deep in the cochlea, a shorter electrode implant may be indicated for stimulation of just the proximal.

Cochlear implants have had a remarkable impact on treatment of severe hearing loss since their first clinical use over 30 years ago. Recent advances have resulted in development of the first cochlear implant system designed for hearing preservation leading to the recent FDA approval of the shorter, Hybrid L24 electrode. This new cochlear implant technology has enabled expansion of cochlear implant candidacy to include patients with high frequency hearing loss but who have near normal low frequency hearing. FIG. 3 shows a "hybrid' cochlear implant ("CI"). The hybrid CI was developed with a shortened 10-19 mm electrode inserted into the basal portion only to allow for preservation of residual low frequency hearing cells.

The Hybrid CI is indicated for mild to moderate hearing loss in the low frequencies and severe to profound hearing loss in the high frequencies (>1500 Hz and less than 60% discrimination scores). The implant uses electrical stimulation in the basal, high frequency section, while protecting the apical, low frequency section, to provide benefit using acoustic stimulation in the apical cochlea segment.

Combining a shortened electrode with conventional acoustic low frequency hearing dramatically improves the outcomes achieved especially for difficult listening situations such as speech recognition in noisy environment or music appreciation. This has expanded the CI candidacy range to include patients with significant high-frequency hearing losses but have normal hearing in the low frequency ranges. However, after implantation of a short electrode into the cochlea, there is often a progressive loss of residual low frequency hearing. In these cases, the patient requires repeat surgery to implant a longer CI electrode in order to stimulate the apical low frequency segment of the cochlea.

Since there is no known method or device today to address this deterioration, if a patient's hearing declines, they require a repeat surgery for electrode removal and exchange with a full length implant in order to stimulate the lost hearing region. This not only subjects the patient to repeated risks of surgery and anesthesia, but it carries a very high risk of causing permanent profound complete hearing loss. In recent Hybrid L24 FDA clinical trials, 22 of 50 patients developed subsequent profound or total low-frequency hearing loss after cochlear implantation with 6 patients undergoing additional surgery to replace the short hybrid implant with a full length standard implant. The FDA determined that the overall benefits of the device outweigh risk for those who do not benefit from traditional hearing aids.

An individual's hearing loss pattern is unique and progresses over time. The current cochlear implants cannot accommodate the natural progression of hearing loss that requires stimulation farther into the cochlea over time due to the fixed nature of a traditional electrode implant.

The target population is patients who have lost high-frequency hearing and consequently have significant difficulty with word understanding, but have too much residual hearing to qualify for a conventional cochlear implant. In these patients, conventional electrode arrays inserted deep into the cochlea typically result in loss of all functional residual acoustic hearing. Recent work has demonstrated the benefits and feasibility of using short electrode arrays in patients who have lost high-frequency hearing but retain residual low frequency hearing.

Current CI electrode arrays have set electrode lengths and insertion depths. Further each cochlea implant company is developing a panel of electrode arrays of varying, but fixed, lengths due to the perceived market demands for electrode arrays of variable lengths. To modify the insertion depth, a repeat surgery must remove the old implant and insert a longer electrode. This not only subjects the patient to repeated risks of surgery and anesthesia, it carries a high risk of causing permanent profound complete hearing loss.

Current CI electrode arrays have preset electrode position determined by the average tonotopic map along the axis of the cochlea length. Static electrode position to hair cell frequency mismatch creates potential for neuronal stimulation mismatch as the individual tonotopic frequencies vary from person to person, leading to lower functional outcomes and poor hearing improvement particularly in the elder who exhibit less central plasticity and diminished ability to adapt to tonotopic mismatch.

Therefore, there is a need to address this hearing decline and the ability to adjust the electrode position within the cochlea following surgery.

SUMMARY

In one embodiment, the present disclosure teaches an implantable system for advancing a cochlear electrode into cochlea. The system may comprise a hollow sheath, drive assembly, and an electrical stimulator. The hollow sheath may have a proximal end and a distal end. The hollow sheath may be configured to house the cochlear electrode. The drive assembly may comprise a main body and a motor. The main body may have a sheath anchor element secured to the proximal end of the hollow sheath. The motor may be disposed inside the main body. The motor may drive the cochlear electrode to move inside the hollow sheath, such as from the proximal end toward to the distal end inside the hollow sheath. The electrical stimulator may be designed for stimulating the cochlear electrode.

Current CI surgery requires the surgeon to manually insert the CI electrode which can cause local trauma to the cochlea wall and hair cells. The invention allows for precisely controlled insertion rates and forces. As a result the perilymph insertion pressure and cochlea wall forces are decreased minimizing damage to the basilar membrane and organ of Corti. The present embodiment would enable controlled, constant and standardized CI insertion rate and forces which would minimize trauma and preserve residual hearing.

In another embodiment, an implantable system may be used for moving an electrode within a patient's body. The implantable system may include a main body, a motor, and a position sensor. The motor may be mounted inside the main body and may be coupleable to the electrode and drive the electrode relative to (such as move away or toward to) the main body. The position sensor may sense the position of the electrode.

In yet another embodiment, the present disclosure discloses a method of remotely controlling movement of an electrode inside a living person's body. The method may be carried out by implanting an implantable system inside the living person's body. The implantable system has a motor. The motor may be coupled to the electrode in such that the electrode may be movable by the motor. The motor may be remotely controlled by a controller outside the body of the living person.

Additional features and advantages of the present disclosure will be set forth in the detailed description, which follows, and in part will be readily apparent to those skilled in the art from that description or recognized by practicing the embodiments described, including the detailed description, the claims, and the appended drawings.

It is to be understood that both the foregoing general description and the following detailed description describe various embodiments and provide an overview or framework for understanding the claimed subject. The accompanying drawings are included to provide a further understanding of the embodiments, and are incorporated into and constitute a part of this specification. The drawings illustrate the embodiments described, and with the description explain the principles and operations of the claimed subject matter.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity or conciseness.

FIG. 5b is a top cross-sectional view of a rotor technique for moving isolated electrode according to one embodiment.

FIG. 8a is a perspective view of a sealable tip connected to the distal end of the hollow sheath.

FIG. 8b is a side-view of a sealable tip according to one exemplary embodiment.

FIG. 8c is a side-view of a sealable tip according to another exemplary embodiment.

Figure 1A:
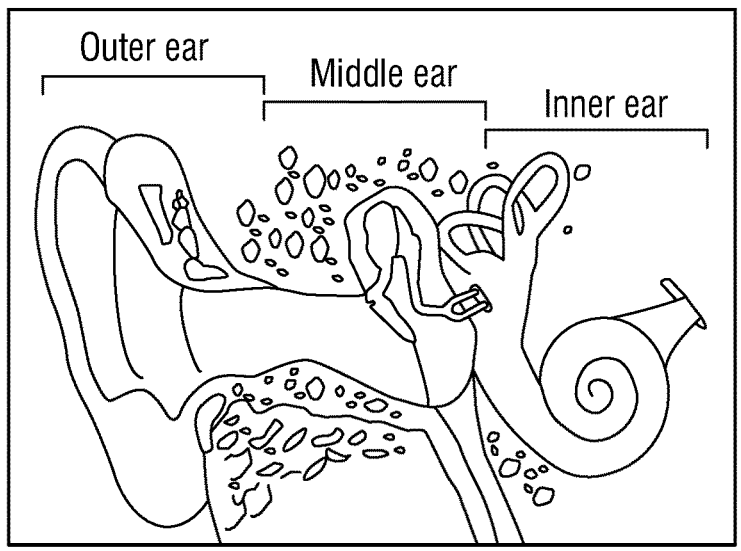
FIG. 1a is a cross-sectional view of an outer ear, middle ear, and inner ear.
Figure 1B:
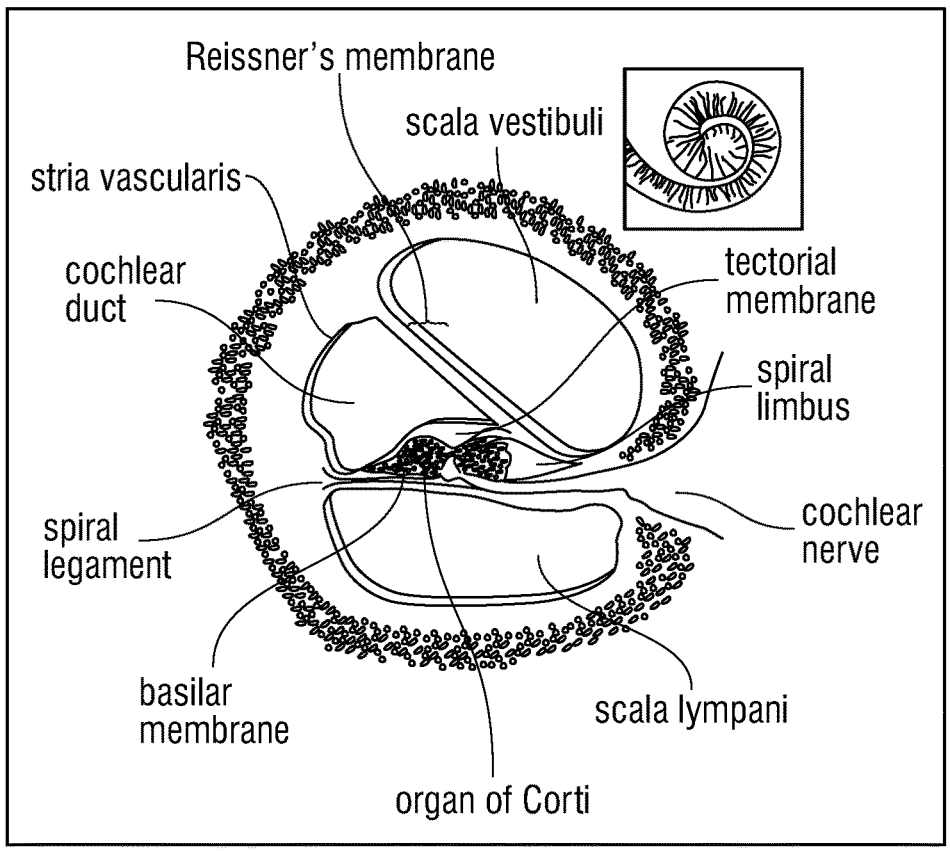
FIG. 1b is a cross-sectional view of cochlea.
Figure 2:
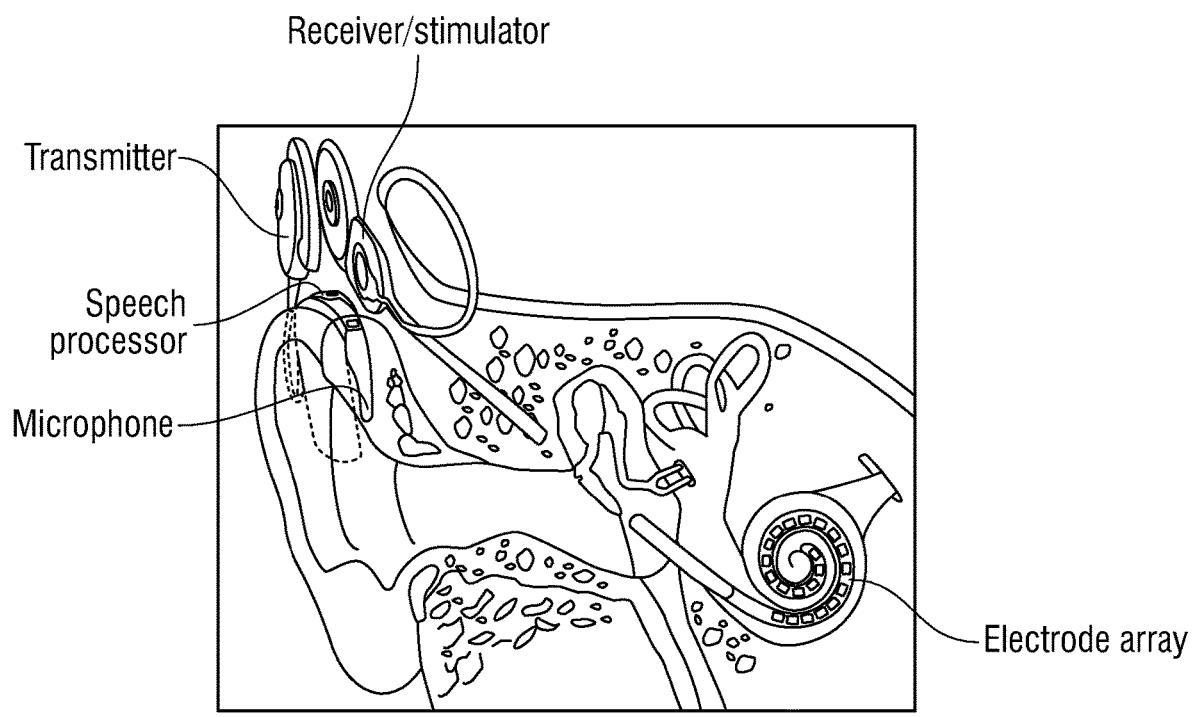
FIG. 2 illustrates a hybrid cochlear implant in use.
Figure 3:
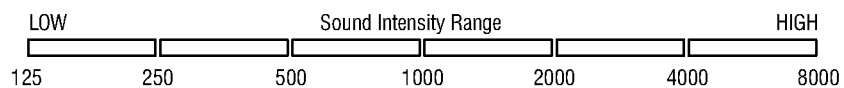
FIG. 3 illustrates a hybrid cochlear implant.
Figure 3:
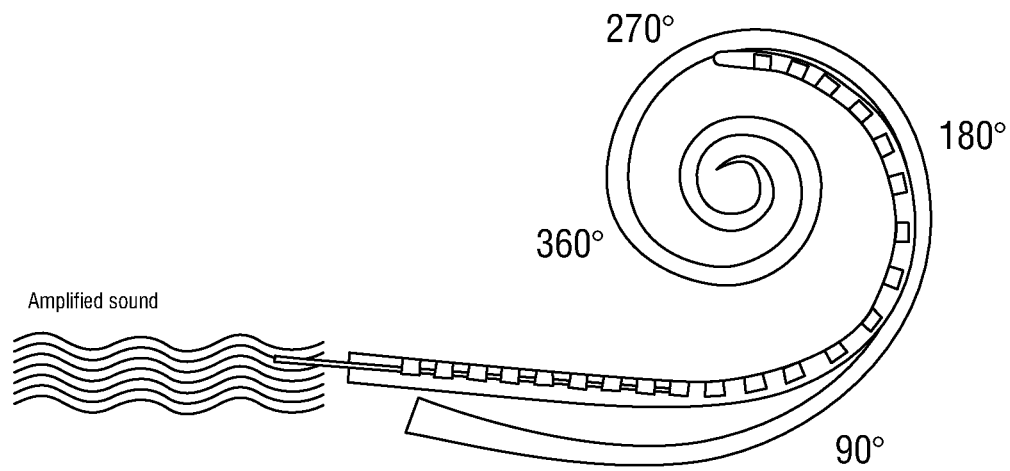

The foregoing summary, and the following detailed description of certain inventive techniques, will be better understood when read with the figures. It should be understood that the claims are not limited to the arrangements and instrumentality in the figures. The industrial design in the figures is one of many ornamental appearances that can achieve the stated functions of the apparatus.

DETAILED DESCRIPTION

The present disclosure can be understood more readily by reference to the following detailed description, drawings, examples, and claims, and their previous and following description. However, before the present compositions, articles, devices, and methods are disclosed and described, it is to be understood this disclosure is not limited to the compositions, articles, devices, and methods disclosed unless otherwise specified and can vary. It is also to be understood that the terminology used is to describe particular aspects only and is not intended to be limiting.

The following description of the disclosure is provided as an enabling teaching of the disclosure in certain embodiments. Those skilled in the art will recognize and appreciate that many changes can be made to the aspects of the disclosure described, while still obtaining the beneficial results of the present disclosure. It will also be apparent that some of the desired benefits of the present disclosure can be obtained by selecting some of the features of the present disclosure without utilizing other features. Those who work in the art will recognize that many modifications and adaptations to the present disclosure are possible and can even be desirable in certain circumstances and are a part of the present disclosure. The following description is provided as illustrative of the principles of the present disclosure and not in limitation thereof.

Reference will now be made to the present preferred embodiment(s), examples of which are illustrated in the accompanying drawings. Using a particular reference character in the respective views indicates the same or like parts.

Unless otherwise indicated, all numbers expressing quantities of ingredients, properties such as size, weight, reaction conditions and so forth used in the specification and claims are to be understood as modified in all instances by the term "about". Unless indicated to the contrary, the numerical parameters in the following specification and attached claims are approximations that may vary depending upon the desired properties sought to be obtained by the invention. At the least, and not as an attempt to limit the application of the doctrine of equivalents to the claims, each numerical parameter should be construed in light of the number of reported significant digits and by applying ordinary rounding techniques, and the figures are not production drawings and should not be construed as necessarily showing all elements to scale.

Various inventive features are described below that can each be used independently of one another or in combination with other features.

Exemplary embodiments may take the form of an entire hardware embodiment, an entire software embodiment (including firmware, resident software, micro-code, etc.) or an embodiment combining software and hardware aspects that may all be referred to as a "circuit," "module" or "system." Exemplary embodiments may take the form of a computer program product embodied in any tangible medium of expression having computer-usable program code embodied in the medium.

Any combination of one or more computer usable or computer readable medium(s) may be utilized. The computer-usable or computer-readable medium may be but not limited to, an electronic, magnetic, optical, electromagnetic, infrared, or semiconductor system, apparatus, device, or propagation medium. More examples (a non-exhaustive list) of the computer-readable medium would include: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner and then stored in a computer memory. In this document, a computer-usable or computer-readable medium may be any medium that can contain, store, communicate, propagate, or transport the program for use by or for the instruction performance system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, and RF.

Computer program code for carrying out operations of embodiments may be written in any combination of one or more programming languages, including an object oriented programming language such as Java, Smalltalk, C++ or the like or any conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any network, including a local area network (LAN) or a wide area network (WAN), or the connection may be made to an external computer (for example, through the Internet using an Internet Service Provider).

Embodiments are described below regarding flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks. The computer program instructions may also be loaded onto a computer or other programmable data processing apparatus to cause operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Broadly, the present disclosure relates to systems and methods for treating sensorineural hearing loss, and to an implantable device and a method of controlling movement of an electrode inside the living person's body. The present disclosure allows the electrode position of an implanted electrode (or any other long, thin implanted medical device) to be adjusted based on the patient's evolving needs without repeat surgical interventions. The technology allows a full length cochlear implant electrode to be partially inserted for preservation of "good" residual hearing. Then, if hearing continues to decline over time, the present embodiment allows a clinician to extend an original full length electrode further into the cochlea to account for the change without surgery. Currently, there are no known devices that would extend a fully implanted electrode after the initial hearing preservation surgery. Patients must choose between continued diminishing hearing and repeat surgery that eliminates all residual hearing. Prolonged hearing loss has been linked to an increased risk of dementia and increased feelings of depression, frustration, anxiety, and social isolation. Hearing loss is second to depression in number of years lost to disability. The present embodiment allows for the adjustment of the cochlear implant electrode array position to stimulate regions of the individualized frequency tonotopic map that have lost hearing while preserving the function of the intact areas of the cochlea. This would enable an individualized treatment regimen. The invention is described in the context of cochlear implants for restoring hearing, but it will be understood that the device can be applied in other implanted device contexts.

The electrode positioning system can provide better patient care at a lower cost by addressing two critical unmet needs. First, the present technology may enhance ability to preserve residual hearing by limiting insertional forces and trauma. It offers the ability to dynamically adjust the depth of an electrode array in-office to best fit a patient's evolving hearing loss over a lifetime with no further surgery. This will reduce overall healthcare costs, significantly enhance the outcomes achieved with current electrode systems, and may significantly expand the cochlear implant candidacy range, adding value for patients, healthcare systems, and implant companies.

A present embodiment may pair with current full length cochlear implants and standard posterior tympanotomy surgical techniques. It may be placed subcutaneously at the time of initial cochlear implantation. The miniaturized micromechanical device may then enable both controlled initial electrode insertion and future nonsurgical cochlear implant repositioning, allowing the cochlear implant to adapt to further hearing decline. The implanted system may remotely move the cochlear implant electrode where it needs to be, when it needs to be there to optimize hearing quality. Initial benchtop studies have demonstrated concept feasibility and insertion forces substantially lower than forces from manual insertion that may lead to decreased cochlear trauma.

The inventors have developed a fully implantable, remotely controllable, and adjustable implant system that allows remote nonsurgical electrode advancement to overcome post-surgical hearing loss and customize the treatment process. The present technology may personalize the treatment regimen for cochlear implant recipients. The device may control and monitor the cochlear implant to enable novel in-office hearing optimization as an individual's hearing evolves with no repeat surgery.

The system may enable partial initial insertion of current full length electrodes for hearing preservation and future nonsurgical advancement as needed to function as a full length electrode. This may provide a significant commercial advantage to the first cochlear implant manufacturer to adopt it for use with their full length implant through a value added product enhancement.

The present embodiment would allow for customized advancement of the implant electrode with no implant removal and reimplantation with a full length electrode. Insertion depth may be customized according to each patient's hearing demands and can be adjusted dynamically according to the patient's evolving hearing needs. In addition, by controlling implantation rate and forces, the present embodiment optimizes the rate of advancement and forces to advance the electrode array to minimize trauma and likely enhance preservation of residual cochlear structures and hearing.

The present implantable position control system addresses a critical unmet need regarding post-surgical hearing loss for patients undergoing hearing preservation cochlear implant surgery. There is no current means to address this problem without additional surgery. The proposed technology overcomes current cochlear implant limitations by allowing wireless, customized, controlled cochlear implant insertion rate and depths at any point during or after initial surgery. These added capabilities will enhance doctor's ability to preserve residual hearing by limiting insertional forces and trauma. It has been established that atraumatic techniques aimed at reducing the insertion force of the electrode during surgery can reduce the inflammation associated with surgery and improve hearing outcomes. Using finely controlled insertion rates, the cochlea insertion forces are decreased minimizing intracochlear damage with the potential to minimize resulting inflammatory response and preserve residual hearing.

The present disclosure further offers the capability to remotely and precisely move an intracochlear electrode. The present implantable system offers the ability to remotely adjust an electrode array depth to best fit a patient's current and changing hearing loss over a lifetime with no further surgery. The envisioned product would insert a full length electrode only a portion of the way into the cochlea to preserve remaining hearing, especially at the mid and low frequencies. Following surgery and if hearing loss progresses, the device could further insert the electrode without surgery to reach the deeper areas of the cochlea. This enables an individualized treatment regimen to accomplish the goal of improved hearing outcomes. Based on the average tonotopic map along the axis of the cochlea length, static electrode position to hair cell frequency mismatch may create potential for neuronal stimulation mismatch as the individual tonotopic frequencies vary from person to person, leading to lower functional outcomes and poor hearing improvement. This is particularly important in the elderly who exhibit less central plasticity and diminished ability to adapt to tonotopic mismatch. Although the electrode stimulation can be adjusted by signal processing techniques, the proposed technology will allow for the adjustment of the physical cochlear implant electrode array position at the discretion of a clinician to best match an individual's physical frequency tonotopic map to the electrical stimulation they received. It offers the ability to dynamically adjust the depth of the electrode array to best fit a patient's evolving hearing loss over a lifetime with no further surgery. Both may significantly enhance the outcomes achieved with current electrode systems, improve cochlear implant hearing outcomes, and enable more people the option of receiving a cochlear implant by expanding candidacy ranges.

Figure 4A:
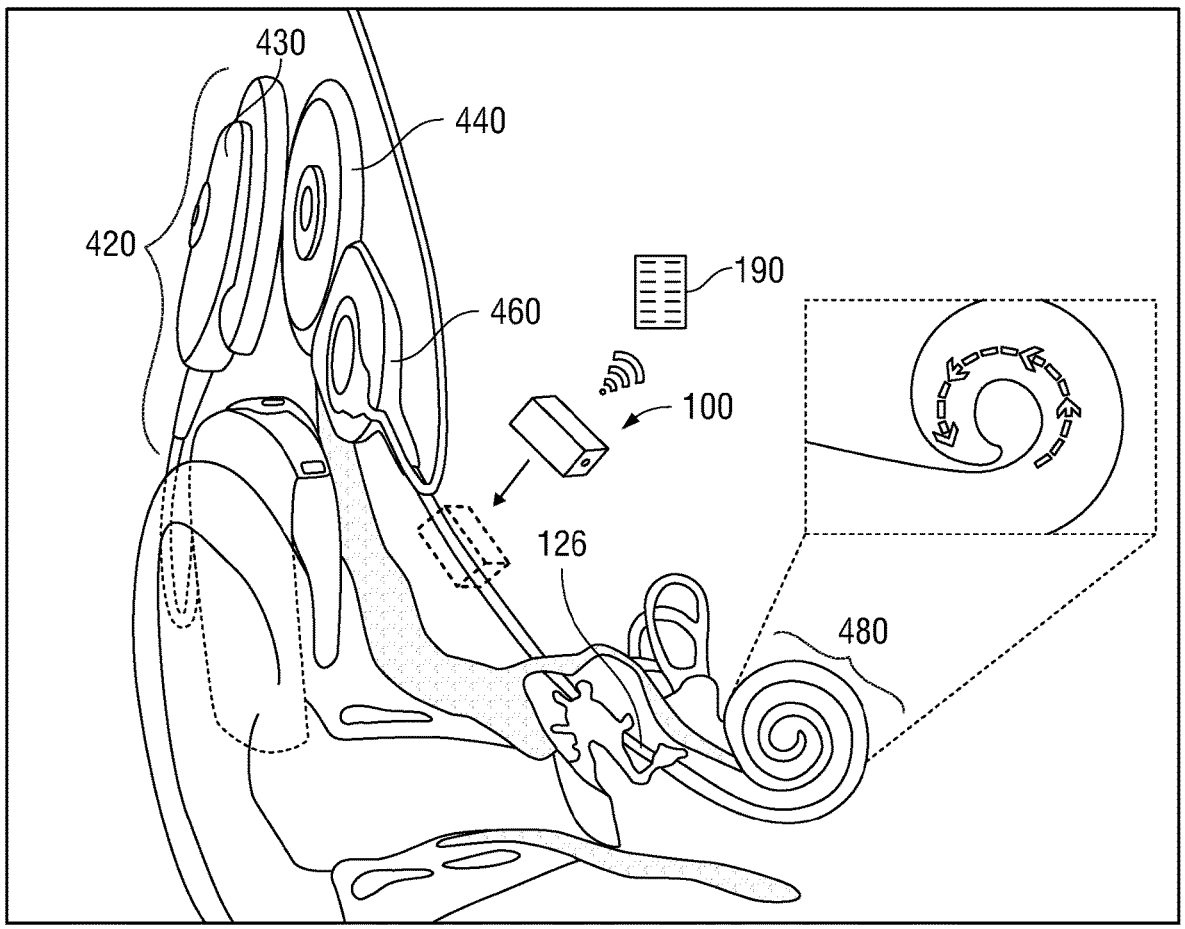
FIG. 4a illustrates an exemplary embodiment of the present disclosure in use for a cochlear implant.

The embodiment provides a modifiable and adjustable treatment of sensorineural hearing loss via user-defined dynamic advancement and feedbacks. The general arrangement for a CI is shown in FIG. 4. The implantable system of FIG. 4a includes an external sound processor 420 and transmitter 430, as is known in the art. The external sound processor 420 communicates through the skin to an implanted coil 440 which is connected to an implanted electrode stimulator/receiver 460. The implanted stimulator/receiver 460 contains sealed electronics and control for an attached electrode 126, which in conventional devices has been manually surgically inserted into the cochlea 480 to a desired distance. In the present disclosure, a motor is enclosed in an implantable system 100.

An insert in the FIG. 4a further shows the movement direction of the electrode inside the cochlea. The implantable system 100 may control and monitor the position of the electrode within the cochlea by moving in a linear path while tracking electrode insertion distance. The system control may be accomplished via a remote communications through an external interface unit (a controller 190) using a low energy communication spectrum such as near field communication (NFC) or radio frequency (RF). The near field communication is a wireless communication standard that enables two devices to establish a communication channel in a short range and period of time using radio waves in the 13.56 MHz frequency range. This may enable three-tiered security features including separate on-off access key/unit, close proximity (<10-20 cm) communication only, and secure access to an external user interface unit (i.e., such as the controller 190).

Figure 4B:
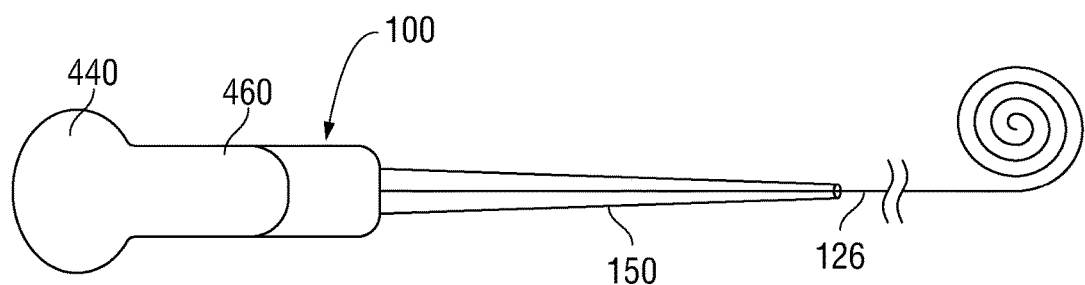
FIG. 4b illustrates another exemplary embodiment of the present disclosure in use for a cochlear implant where the implantable system is integrated with a receiver/stimulator.

In one embodiment, the implantable system 100 may be standalone and separate away from the stimulator/receiver 460. In another embodiment, as shown in FIG. 4b, the implantable system 100 is sealed and may be formed as a compartment in the implanted electrode stimulator/receiver 460. The motor includes an implantable mechanical positioning unit to insert the electrode or as means to make positional adjustments after implantation and surgical site closure. The implantable device 100 may be controlled using an implanted electronic control unit capable of electrode array position adjustment and may be controlled with an external, nonsurgical controller 190. The nonsurgical controller 190 may be advantageously combined with the existing communications and used to control the implanted stimulator 460 in an integrated device. The controller 190 may be accessed externally via remote connection or with a device near the surface of the skin. The technique allows for control, modification, and monitoring of the electrode array position after implantation using an external means. This could entail mapping the individual's tonotopic hearing loss pattern and tailoring the electrode array implant position accordingly at any point in time after surgical implantation.

Figure 5A:
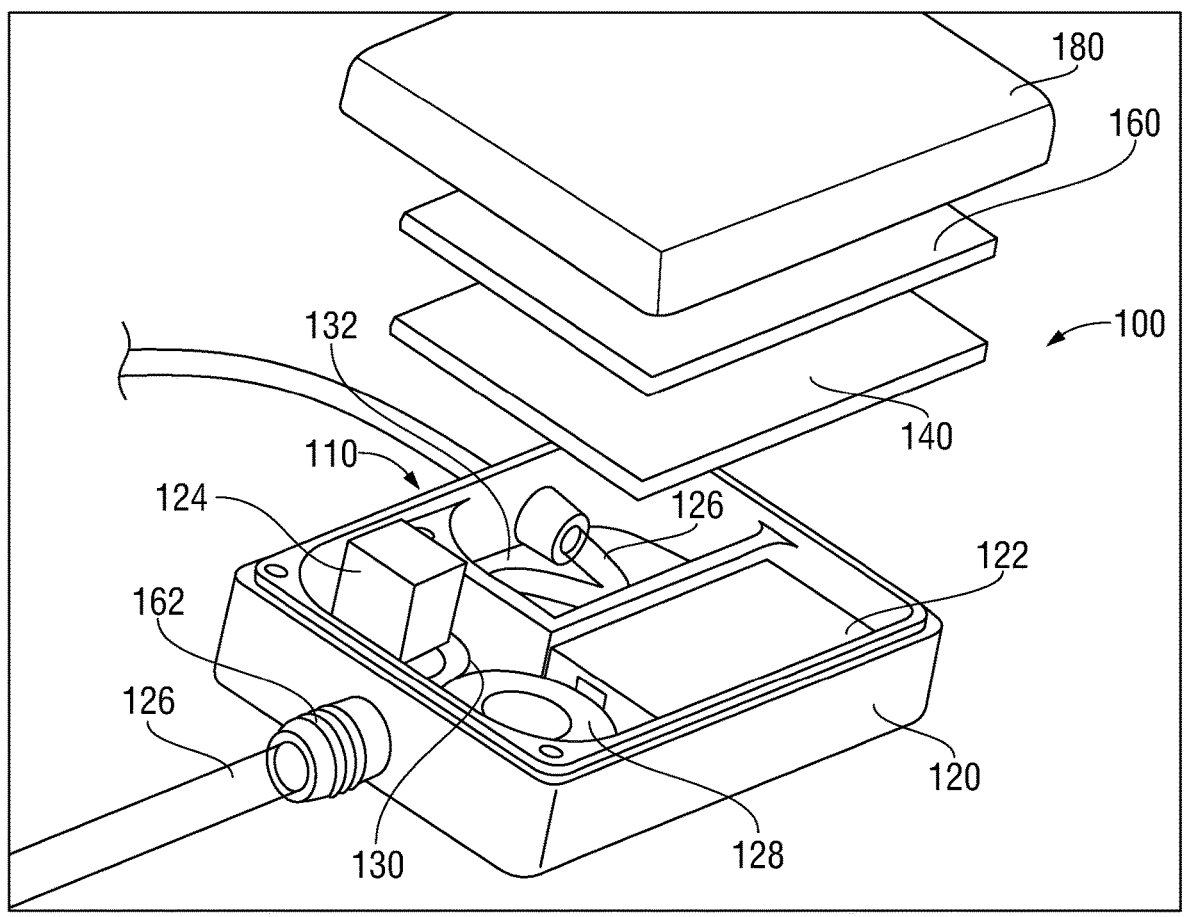
FIG. 5a is an exploded view of an implantable system for a cochlear implant according to one embodiment.

As shown in FIG. 5, the implantable system 100 may be configured for moving an electrode 126 within a patient's body. The implantable system 100 may be used for advancing a cochlear electrode into the cochlea. The implantable system 100 may include a drive assembly 110. The drive assembly 110 may have a main body 120, a motor 122, and a position sensor 124. The motor 122 may be mounted inside the main body 120 and coupled to the electrode 126, such as a cochlea electrode. The motor 122 may drive the electrode 126 to move relative to the main body 120, such as away from or closer to the main body 120. For a cochlear implant, the volume available in the typical location for an implant to house the motor 122 may be limited to a maximum of roughly 3.2 cm×2.4 cm×3.7 cm, however in the designs contemplated the motor assembly may be realized in a volume of approximately 2.5 cm×2.5 cm×1.25 cm or smaller, and further reductions may be had by integrating the motor into the electrode stimulator housing. It will be appreciated that the figures accordingly are for illustration and are not necessarily to scale. The motor may have peak force from about 0.01 N to about 10 N. The resolution of the motor may be from about 100 nm to about 1,000 nm. The stroke length may be from about 1 mm to about 100 mm. The voltage run for the motor may be from about 0.1 V to about 10 V. There may be no power consumption when the motor rests. The motor 122 is advantageously magnetic resonance imaging compatible, such as a piezoelectric motor.

The motor 122 is mounted in the main body 120 placed in a bony cavity created surgically in the mastoid bone to fit the shape of the motor assembly. Fibrous tissue and new bone growth over time further fixes the motor assembly in place relative to the cochlear implant and the cochlea. Additional spikes, teeth, or protrusions could firmly secure the motor assembly, although it is expected that the opposing force for electrode insertion is small for an electrode floating within the cochlea fluid space. The motor may be constructed of piezoelectric material that has a reversible, linear electromechanical interaction between the mechanical and electrical state. The piezoelectric material in the motor is subjected to electrical stimulation and produces mechanical strain resulting in positional change. This can be harnessed in a rotary or linear motor to generate forces on different drive surfaces.

The motor 122 may be a micro and nano stepper motor or magnetic and nonmagnetic actuator units with a noncaptive stepper motor. The motor may be capable of controlled rotation and horizontal advancement or withdrawal. In one embodiment, the piezoelectric motor may have one axis. In another embodiment, the piezoelectric motor may have two axes. A first portion of the motor may operate to control depth. A second portion may operate to control axial rotation.

The motor 122 may contain a means, such as a position sensor 124, to monitor electrode position within the insertion site. The position sensor 124 may sense the position of the electrode 126, monitoring its advancement position. The position sensor 124 may be configured to connect to a pulley wheel 130 with a textured surface. The electrode array may be capable of rotation to optimize electrode array placement near auditory neural elements. The electrode array housing may be encased in a protective hollow sheath or may telescope to prevent fibrosis from inhibiting subsequent advancement. The travel range of the CI electrode array may be from about 1 mm to about 30 mm. The control motor may be capable of micro step advancements. The electrode may be inserted initially manually in the standard fashion and then may be connected with the control motor and unit for subsequent mechanical, controlled, monitored final insertion either after surgical closure or during initial surgical intervention. Control of rotation is important for navigating the electrode through the spiral cochlea, as the electrode may be pre-curved and the ability to twist the electrode as it is moved can assist insertion with minimal damage to residual hearing. The electrode can engage with the driving surfaces either directly, or with an adaptor such as a sleeve or rod that the electrode is in contact with.

The main body 120 may further include a drive wheel 128. The drive wheel 128 may be made of MRI compatible materials, such as ceramic. The drive wheel 128 may be driven by the motor 122. Instead of a drive wheel, the motor drive surfaces can be screw threads, gears, electrically stimulated bending "fingers", magnets, or other style of actuator surface that may either directly engage the electrode or engage an adapter or carrying member that the electrode is in sufficient friction or fixed contact with such that the electrode is advanced.

The main body 120 may further include a cover 180 so the main body 120 is hermetically sealed. The main body 120 further has a housing partition 132. The housing compartment 132 is configured to store the electrode 126. The main body 120 may further include an RF controller and transceiver (not shown) for establishing a wireless link between the implanted motor and an external monitor/control device.

The implantable system 100 may be powered transcutaneously using implanted rechargeable components such as a supercapacitor or a battery 160. The battery 160 may be charged wirelessly by a wireless controller 190 using near field communications (NFC) or radio frequency (RF). Power may be transferred transcutaneously to a subcutaneous unit charging an implanted supercapacitor or battery. The typical motion may consume about 300 mW. However, the wireless communication without motion may consume about 10 mW. The charge vs. move time ratio may be from about 30:1 to about 100:1. Typical wireless motion at 500 um/sec over a total distance of 10 mm may take about 200 second (3.3 min) with charge-discharge incremental motion. The wireless communication is based on ultra-low power multiprotocol SoC (system on a chip) NFC or Bluetooth low energy communication. The main body 120 may further include a circuit board 140. The wireless controller 190 may be configured to control the motor 122. The electrode 126, such as cochlear electrode, may be coupled to a speech processor (shown in FIG. 4).

The motor 122 may be isolated from the rest of the electronics. The motor 122 and the associated controls may conduct electricity and therefore needs to be sealed from fluids and leakage in separate sealed compartments as with other electronics.

In one embodiment, one method includes bonding a flexible polymer material such as silicon around the motor housing and the outer circumference of the piezoelectric drive tip, leaving only a ceramic tip exposed. This may seal the entire motor 122 so that the electrical conductive piezoelectric material may be isolated from fluid exposure. This also allows the inert ceramic tip to be mobile and exposed within the encasement. The flexible polymer permits the ceramic tip to ultrasonically vibrate and move with the surrounding seal while still maintaining direct frictional contact with the ceramic drive wheel.

Ideally, the main body and components within the main body may be sealed from fluid exposure or leakage. To allow the electrode to move in and out of the motor housing area without leakage into the control unit case over time, a valve-like compression seals and gaskets may be designed at the control unit case exit opening and along the hollow sheath 150. Multiple seals may be placed in series along internal length of sheath. These valves seal by compressing against the electrode carrier material to create fluid-tight seal yet still allow the electrode to pass through when moving in or out. The valves also allow for a variety of electrodes outer diameter dimensions to pass through while still maintaining compression and a fluid-tight seal.

Figure 5C:
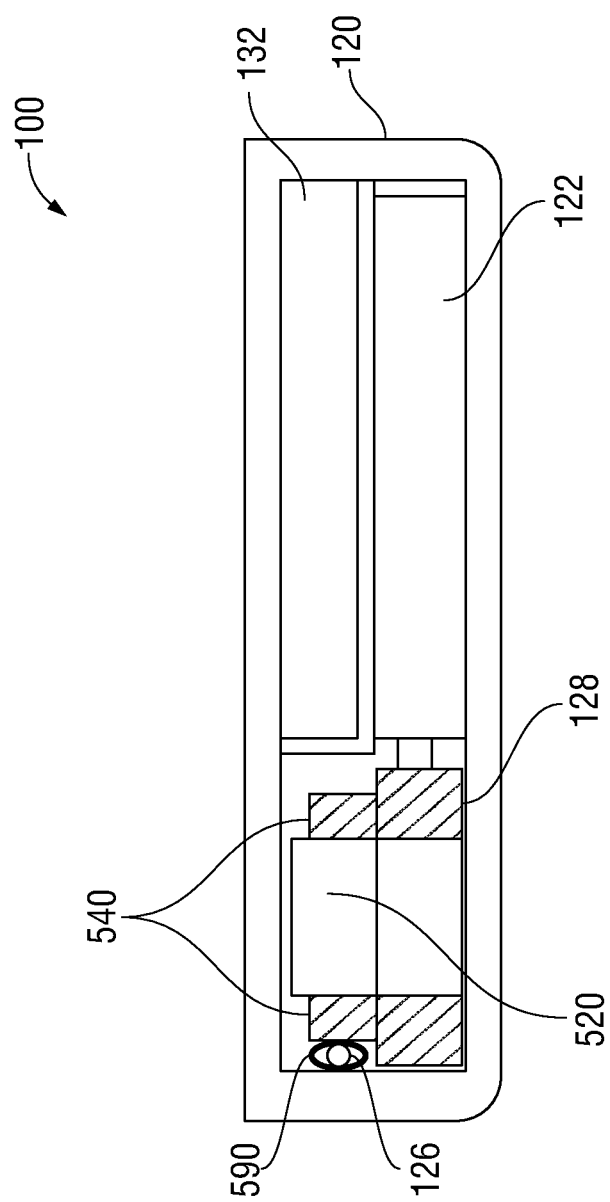
FIG. 5c is a side cross-sectional view of a rotor, drive wheel, motor, and housing partition according to another embodiment.

The above method requires good friction seals to isolate from body fluids. Another contemplated method that allows complete isolation of all motion components and electronics with no movable seals translates rotary motion through a fixed polymeric compressible and stretchable sheath 580 to the freely mobile electrode 126 within by a peristaltic pump type mechanism of motion as shown in FIG. 5b or 5c.

FIG. 5b shows a top cross-sectional view of a rotor technique for moving isolated electrode according to one embodiment. The sheath inner opening is bonded and fixed both at the inner "excess electrode housing" opening 570 and to the "electrode exit opening 590." The compressible sheath 580 may transverse through the encasement and may join with a hollow sheath 150. Within the sealed unit encasement—the main body 120, a rotor 520 with multiple rollers or wipers 540 attached to its external circumference, i.e., the drive wheel 128, compress onto the flexible polymeric compressible sheath 580 which in turn compresses and "grabs" the floating electrode 126 housed within the compressible sheath 580. As shown in FIG. 5c, which is a side cross-sectional view of a rotor, drive wheel, motor, and housing partition according to another embodiment, as the motor 122 turns the rotor 520 and the compressing roller/wipers 540 revolve, the electrode 126 may translate and move linearly within the compressible sheath 580. The repeated cycles of compress, translate, and release advances the electrode. On each cycle, the sheath 580 relaxes to its starting position without pulling back the free floating electrode as it is released by the roller/wiper. The rotor 520 may be attached or fixed coaxially to the drive wheel 128 in such that as the drive wheel 128 turns the wiper rotates. The rotor 520 and the drive wheel 128 may be a single piece. Alternatively, the rotor 520 may be a separate piece from the drive wheel 128. Any fluids that advance into the housing through sheath 150 and find their way into the compressible sheath 580 are confined to the interior of the sheath, which is sealed to a compartment wall at the point where the electrode is electrically connected by a hermetically sealed electrical connection to the electrode electronics.

Figure 6A:
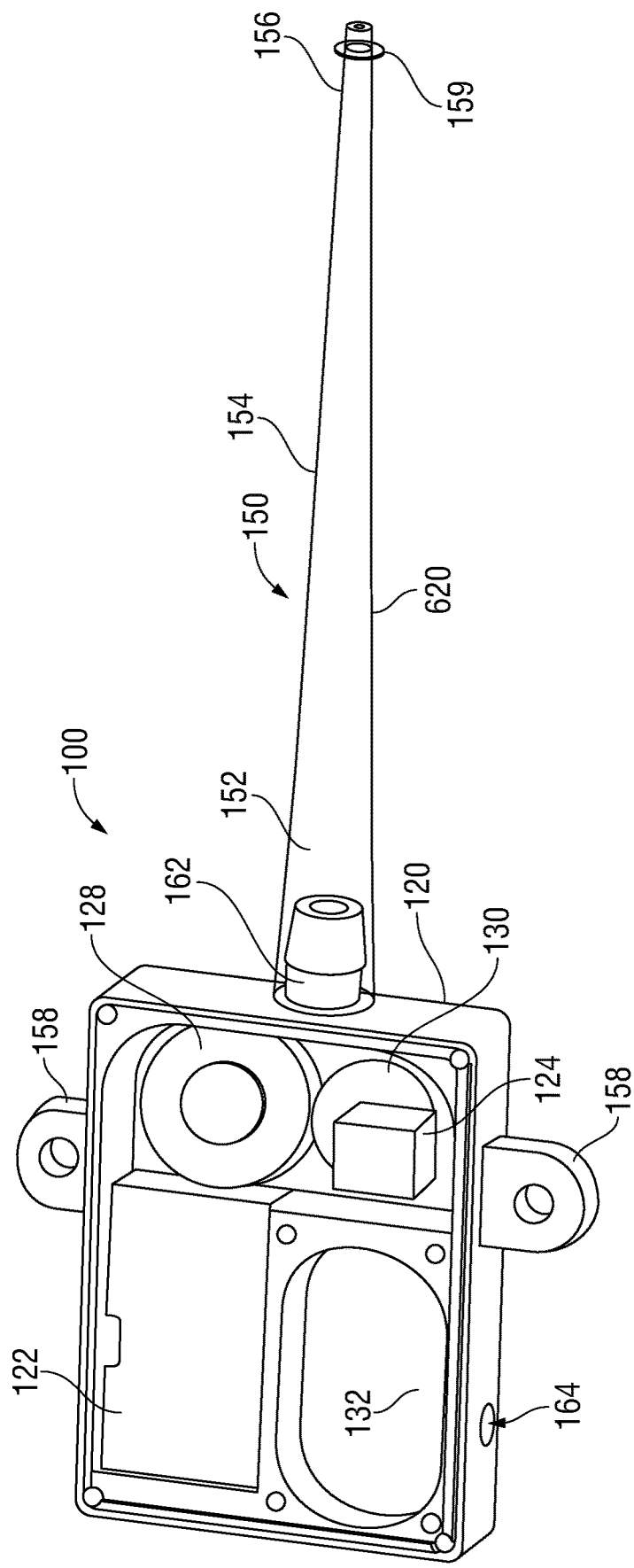
FIG. 6a illustrates an exemplary embodiment of a main body without a cover for clarity purpose.

As shown in FIG. 6a, the implantable system 100 may further include a hollow sheath 150. The sheath 150 protects and stabilizes the electrode in the cavity between the motor or implant electronics housing and the entry into the cochlea. The hollow sheath 150 may have a proximal end 152, a middle part 154 and a distal end 156. The distal end 156 may slide within the middle part 154 of the hollow sheath. The hollow sheath 150 may be configured to house the electrode 126 (shown in FIG. 5). The main body 120 of the drive assembly 110 may have a sheath anchor element 162 (also shown in FIG. 5). The proximal end 152 of the hollow sheath 150 may be connected to the sheath anchor element 162. The initial proximal end 152 may couple to the main body 120 for a hermetic or water tight seal. This may be achieved through direct fusion with the case material, screw, barb, clamp, or other means to seal the tubing to the case. The proximal portion may be tapered from the initial larger diameter to smaller mid or distal diameters. It may include a clear portion to visualize the inner electrode or filaments. The motor 122 may drive the electrode 126 to move inside the hollow sheath 150, such as from the proximal end 152 toward the distal end 156 or from the distal end 156 to the proximal end 152 inside the hollow sheath 150. The hollow sheath 150 may further include a taper 620 from the proximal end 152 to the distal end 156. The interior space of said sheath may be isolated from fluid communication with any portion of the main housing by extending said sheath through the motor housing such that all spaces occupied by said electrode in the main housing may be isolated from fluid communication with the spaces housing said motor.

The main body 120 may further include a plurality of fixation flanges 158 outside the main body (i.e., at both sides of the main body 120). The flanges 158 may fix the main body 120 to the bones of a patient's body. The main body 120 further includes an electrode insertion opening 164. The main body 120 may store a portion of the electrode. More specifically, the electrode 126 may be inserted into the housing partition 132 that stores a portion of the electrode 126, such as cochlear electrode, via the electrode insertion opening 164. It will be appreciated if the housing 120 is integrated with the electrode stimulator electronics, the proximal portion of the electrode will terminate in an electrical connection that is hermetically sealed and passes to the stimulator electronics, eliminating the opening 164.

The electrode 126 may be inserted from the housing partition to an area between the drive wheel 128 and the pulley wheel 130 to the hollow sheath 150. The electrode 126 may be pinched between two wheels and may move when the drive wheel 128 turns by the motor 122. The distal end 156 of the hollow sheath 150 may have a sealing disk/gasket 159 outside the hollow sheath so liquid or solid materials may not move to the main body 120.

The hollow sheath 150 may be a fully implantable sheath. The hollow sheath 150 may house the electrode, guide insertion, direct motion of the electrode, and prevent surrounding tissue formation and fibrosis which would hinder future electrode or filament movement. The hollow sheath 150 may be envisioned to serve as future means for liquid therapeutic delivery via a double lumen or single lumen design in which therapeutic agent surrounds internal electrode housing or flows through a separate divided channel into the cochlea.

TABLE 1

| Sheath | OD | ID | Length | Wall | Notes |
| --- | --- | --- | --- | --- | --- |
| Experimental Test tubing | 1.5-1.8 mm | 1.3-1.6 mm | — | 0.1-0.5 mm | PTFE lined, Polyimide composite, Non-ferromagnetic coil reinforced |
| Total Extracochlear | 1.5-1.8 mm | 1.3-1.6 mm | 44-55 cm | 0.1-0.5 mm | Adjustable, thin, clear, flexible, maintains lumen |
| Proximal 1st | 1.5-3.5 mm | 1.4-3.1 mm, tapering to 1.3-2 mm | 8-22 mm | 0.1-0.2 mm | Tapers, Stretch over barb/sealed to unit, Clear |
| Mid 2nd | 1.8-3.1 mm | 1.4-2.0 taper to 1.3 mm | 8-22 mm | 0.1-0.2 mm | Flexible, kink resistant@90 deg radius 1.5 cm, low internal friction |
| Distal 3rd | 1.0-1.5 mm | 1.0-1.3 mm | 1-8 mm | 0.1-0.2 mm | Clear, adjustable or cut to fit |
| Intracochlear Tip | 1.0-1.5 mm | 1.3-1.0 taper to 0.8 mm | 1.0-1.5 mm | 0.1-0.2 mm | Soft, Flexible, Polyimide/Silicon, Biocompatible |

The hollow sheath 150 may be made of a biocompatible materials, such as polymeric (polyimide, polytetrafluoroethylene (PTFE), silicon), thermoplastic, metals, or composite materials (non-ferromagnetic coil or braid reinforced) which can be permanently implanted for up to 30 years or more with representative dimensions in table 1 above. Although one continuous unit, the sheath length may have varying physical properties along its length to meet specific needs of the envisioned application, for example, cochlear implant electrode insertion and positioning. The tube structure is kink-resistant yet flexible. One embodiment incorporates composite non-ferromagentic wire coils/braids into walls to maintain luminal space while implanted.

The internal sheath surface may be lined with functionalizing materials for decreased internal friction such as PTFE or include inner features protruding into inner lumen such as linear grooves, pattern, rings or guidance tracks. These internal luminal surface features have several functions such as decreasing inner surface friction, guide moving electrode/filament to maintain specified configurations (i.e. rotational or spatial relationship) or preventing passage of intraluminal fluids or materials.

Figure 6B:
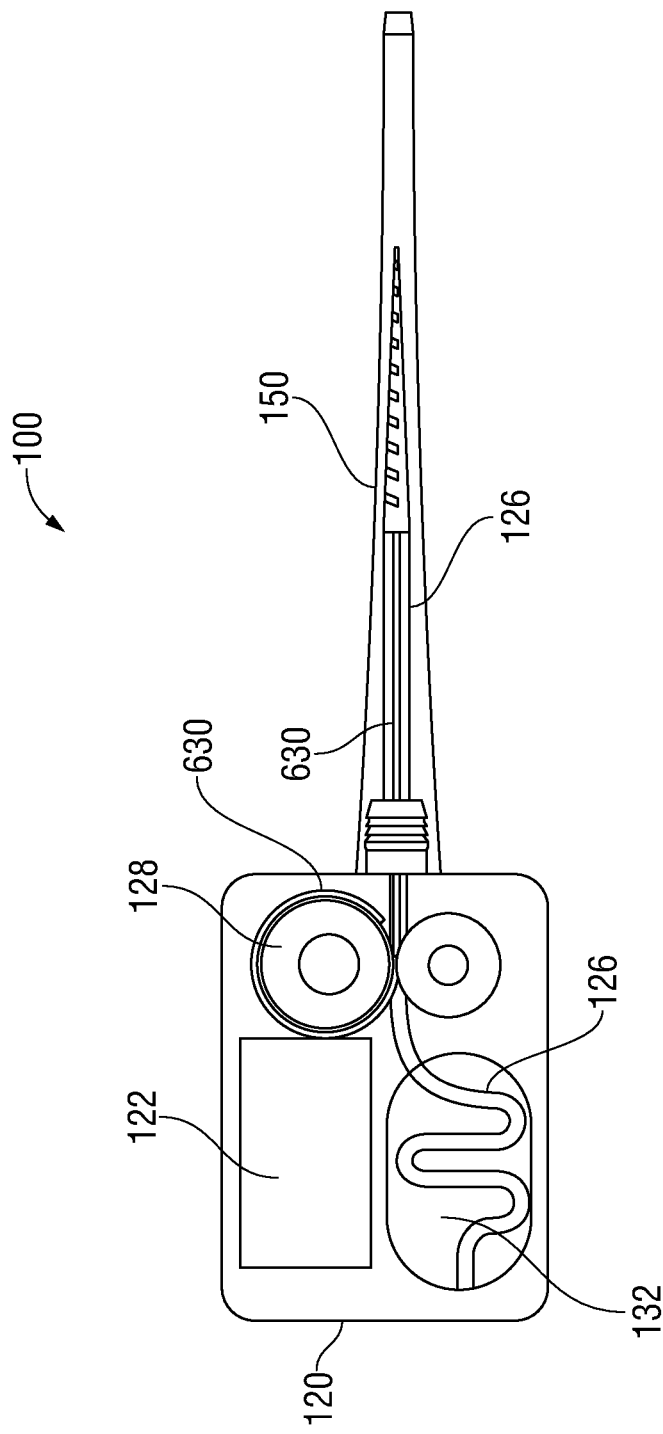
FIG. 6b illustrates a top cross-sectional view of a main body, a hollow sheath, and an electrode according to one embodiment.
Figure 6C:
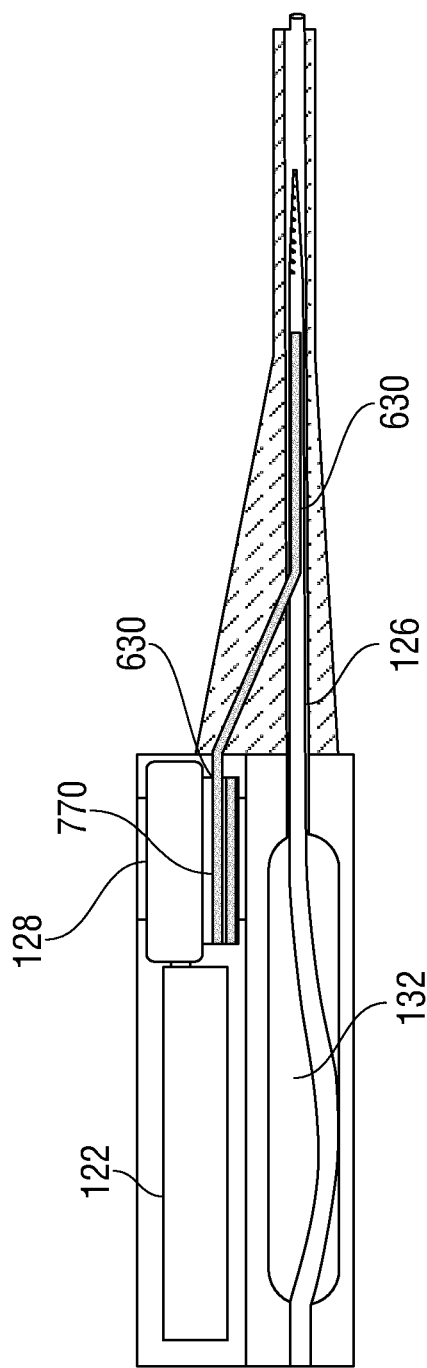
FIG. 6c is a side cross-sectional view of guide wire with a spool, motor, drive wheel and electrode according to yet another embodiment.

As shown in FIG. 6b, the electrode 126 may be pushed by a guide wire 630, such as an insertion guide wire. The excessive guide wire 630 may be coiled around the drive wheel 128 and may be advanced as needed and carrying the electrode 126 with it. In another embodiment, as shown in FIG. 6c, the guide wire 630 may be wound around a spool 770 that is coaxial with the drive wheel 128. In further another embodiment, the excess guide wire 630 may be housed in a housing compartment (not shown) which may be similar to the housing partition 132 that stores the excess electrode 126.

In one embodiment, an electrode 126 may be paired with multiple guide wires 630 and the motorized control of multiple electrode guide wires for controlled insertion geometry. Multiple guide wire channels within the electrode may allow for guide wires of varying stiffness and geometry. If a straight guide wire is stiffer than an adjacent curved memory alloy wire, the electrode may remain straight if the stiff wire and curved memory alloy wire are in similar positions. To place the electrode along the cochlea curvature, the stiff guide wire may be retracted by the motor control units at the point of desired curvature, allowing the curved guide wire to assume its shape within the cochlea. The curved guide wire may then advance the electrode to the desired position along the cochlea using the implanted motor control unit. Multiple memory alloy wires may optimize cochlear electrode placement.

The guide wire retraction order and distance may be programed into the motor control software to provide customized insertion based on patient's individual anatomy and hearing needs. This would minimize trauma to the cochlea during insertion.

The subsequent connection to the implantable system may be accomplished by reversible, interchangeable replaceable connection. In the event of the need for CI electrode exchange, the implantable system may remain in place and the electrode array may be replaced without removing the motor, drive wheel, position sensor, and a pulley wheel. The new electrode may be reconnected with the implanted mechanical and control units.

Figure 7A:
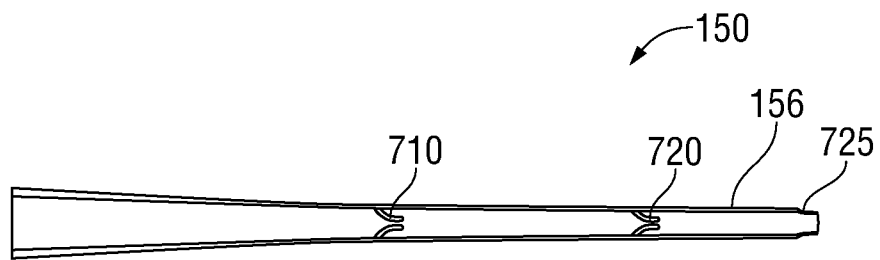
FIG. 7a is a cross-sectional view of a sheath according to one embodiment.
Figure 7B:
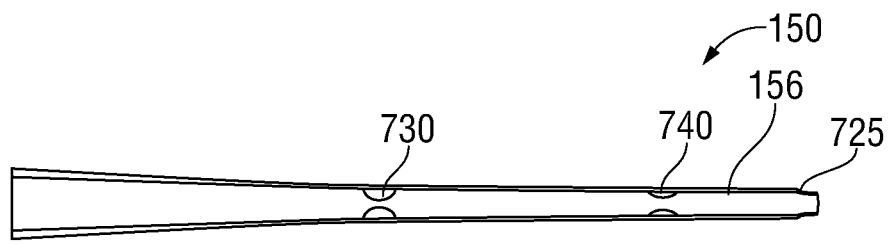
FIG. 7b is a cross-sectional view of a sheath according to another embodiment.

As shown in FIGS. 7a and 7b intermittently spaced internal valves 710, 720, 730 or 740 or a ring gasket 159 (as shown in FIG. 6) form water tight seal around the internal electrode/filament wire to prevent backflow of any fluid or material retrograde to main body. The valves or inner septum are composed of a thin elastic polymeric material which does not impede the inner electrode/filament movement or significantly increase frictional forces yet creates a water tight seal with the electrode and the more distal lumen.

The middle part 154 of the hollow sheath 150 has increased flexibility up to 90 degree kink resistant radius while maintaining luminal internal shape and wall rigidity. As in Table 1 above, inner and outer diameters taper to the dimensions of the distal third of the sheath.

The distal end 156 of the hollow sheath 150 may include an adjustable length portion with representative dimensions in table 1 above that may be modified in length to fit varying anatomical requirements. The length may be modified by various means yet still maintain a water tight seal from the surrounding environment. The sheath may be premarked for precise material removal by cutting to a desired length. In another embodiment, the length is increased or decreased by repeated small folding of the walls in an "accordion-like" movement of the walls as needed to meet individual anatomical requirements. In another embodiment, the sheath length may be increased or decreased by intussuscepting the walls so the distal luminal wall moves within the larger proximal lumen as one unit without interrupting the continuity of the inner and outer luminal integrity or seal. In the further embodiment, the distal end portion slides within the proximal larger lumen so the inner diameter of the proximal lumen matches or is slightly smaller than the outer diameter of the distal sheath for a water tight seal yet still allows for sheaths to slide to adjustment.

As shown in FIGS. 7a and 7b, the hollow sheath 150 may further have a sealable tip 725 at a terminal end of the distal end 156 of the hollow sheath 150. The sealable sheath tip 725 has the exemplary dimensions in Table 1 above and functions as an adapter and transition from larger to smaller inner and outer diameters to fit the round window opening or a surgical cochleostomy. The proximal lumen inner diameter of the terminal tips serves as a hard stop fail safe to prevent electrode insertion past maximal desired insertion distance. The terminal tip 725 may be conical shaped to facilitate penetration of the round window membrane.

As shown in FIG. 8a, the sealable tip 730 may have a slit 750 in an outer surface 740. To meet the functional goals, the tip material and mechanical properties have been tailored to be stiff in the longitudinal direction at the tip yet compression flexible radially. This may be achieved by longitudinal slits (from about 3 slits to about 12 slits, preferred 8 slits) evenly spaced in the distal terminal conical tip which create flexible tabs of material. When point forces on the conical tip are directed retrograde or proximally, as in during penetration of the round window membrane, the multiple segments maintain their overall pointed integrity. However, when inner luminal electrode/filament moves antegrade or distally through the lumen and conical tip, the flexible slits in the conical tip allow to expand the circumferential segments to accommodate the electrode passage. This expandable feature of the conical tip may allow for device use with a range of electrode diameters and sizes to pass through distal tip into the cochlea. In one embodiment, as shown in FIG. 8b, the sealable tip 725 may have a tip opening 760 at the center. As shown in FIG. 8c, the tip opening 760 may be offset from the center to guide the electrode to a desired round window opening quadrant region to minimize insertion trauma and contact with intracochlear structures. Tapering of the tip allows for size variation in round window or surgically created cochleostomy.

In another embodiment, the sealable tip 725 may not incorporate a conical tip but instead the inner diameter is tailored to closely fit the outer diameter of the intracochlear electrode. It could be envisioned to incorporate an opening for a second lumen for intracochlear therapeutic delivery. This sealable tip 725 protrudes into the cochlea from about 1 to about 1.5 mm. Therefore, the distal tip is composed of a biocompatible material to prevent or minimize any intracochlear inflammatory response. Similarly, to minimize any intracochlear material response, the sealable tip 730 may be coated in thin films or antifouling agents which reduce fibrotic tissue formation around the site. In one embodiment, the sealable tip is composed of silicon. In another embodiment, the sealable tip may be a thin walled polyimide, but it could be made of any polymer, metal, or composite biocompatible material.

The interface between the distal tip outer surface and bony round window opening is a potential location for fluid leakage and sealing. The current embodiment incorporates the ring gasket 159 (shown in FIG. 6) of thin material that functions as a stopper to plug region around sheath and round window or cochleostomy. The material may be synthetic material either bio-resorbable or permanent. In both instances, the material and material structural microarchitecture scaffold that encourages tissue ingrowth to create a tissue plug using body's own ingrowth of cells and tissue formation.

The implantable system 100 may contain force sensors within an integrated sensor (not shown) that controls the amount of force applied via closed loop feedback mechanism to control insertion after implantation including means for safety fail safe stop. This would sense the force feedback on the cochlea wall and surrounding structures with safety stop command if force limit is exceeded. The implantable system 100 may further include integrated sensors also capable of real-time force sensing and position feedback. The integrated sensors may also be capable of monitoring hair cell and neuronal membrane voltage.

Figure 9:
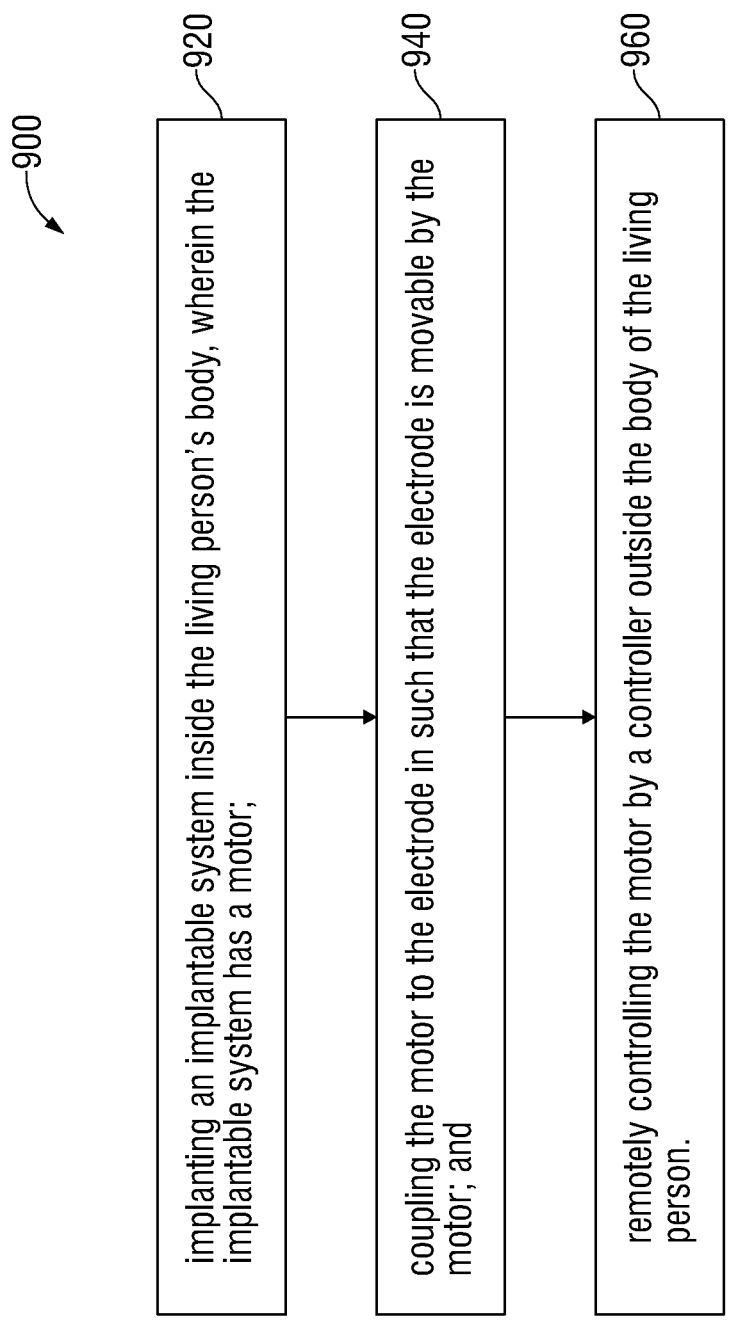
FIG. 9 is a flow chart illustrating a method of remotely controlling movement of an electrode inside a living person's body.

As shown in FIG. 9, the present disclosure teaches a method 900 of remotely controlling movement of an electrode, such as a cochlear electrode, inside a living's person's body. The method may be carried out by implanting an implantable system inside the living person's body in a step 920. The implantable system has a motor. The motor may be coupled to the electrode in such that the electrode may be movable by the motor in a step 940. The motor may be remotely controlled by a controller outside the body of the living person in a step 960. Optionally in any embodiments, the implantable system may have a main body, where the motor, such as a piezoelectric motor, is mounted inside the main body. The implantable system may have a hollow sheath. The hollow sheath may have a proximal end and a distal end. The proximal end of the hollow sheath may be secured to a sheath anchor element of the main body. The hollow sheath may further have a sealable tip at a terminal end of the distal end. The sealable tip may have a slit in an outer surface of the sealable tip. Optionally in any embodiments, the hollow sheath may be sized to house the electrode and have a taper from the proximal end to the distal end. The main body may further include a drive wheel driven by the motor and a housing partition configured to store the electrode.

Optionally in any embodiment, the main body may have an energy source, such as a battery and a position sensor. The position sensor, such as a potentiometer or Hall sensor may be configured to connect to a pulley wheel with a textured surface so that the implantable system can monitor or control the position of the electrode. The method 900 may further include remotely charging the energy source, such as the battery inside the main body wirelessly and coupling the electrode to a speech processor.

The method 900 may further include sending real-time remote data to a user including data on insertion forces, insertion position/length, surrounding electrical resistance and potentials, and rate of advancement during insertion for monitoring. The control functions need not be integrated in the position sensor but may be distributed to the receiver/stimulator or other portion of the device with adequate space to house the control functions.

In an exemplary method, the implantable system 100 may contain a manual override mechanism in which the surgeon may manually insert the electrode using a mechanism including dial turn, screw, or direct insertion using standard soft insertion techniques. The device may then be connected and integrated with the implantable system and allow the system to be adjusted further via the controller described previously after implantation.

EXAMPLE I

Figure 10C:
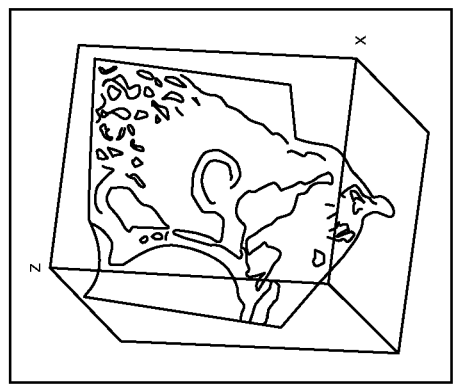
FIG. 10c is a representative microCT image of human temporal bone with cochlea midmodiolar axis view.
Figure 10B:
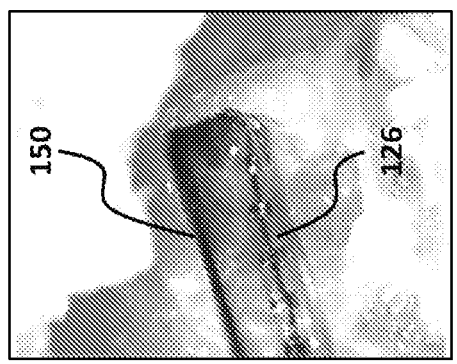
FIG. 10b illustrates an image of an electrode insertion sheath in cadaver round window.
Figure 10A:
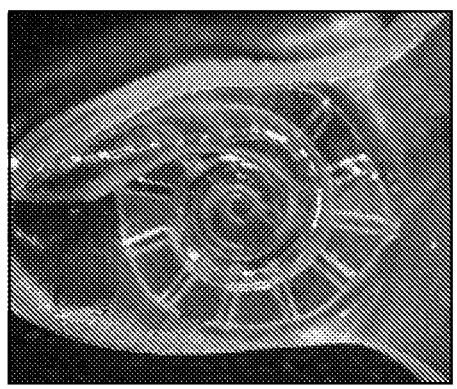
FIG. 10a illustrates an image of electrode inserted in a phantom cochlea model.

A benchtop model has been used to establish proof of concept using components that are scalable and miniaturizable for subsequent development of an implantable robotic position system for cochlear implant electrode position control. Through preliminary studies in both 3D printed cochlea models and human cadaveric temporal bone insertion testing, the ability to reposition an intracochlear electrode has been demonstrated. (FIG. 10a-10c). FIG. 10a shows an image of electrode inserted in a phantom cochlea mode. FIG. 10b shows an electrode insertion sheath in a cadaver round window. FIG. 10c is a representative microCT image of human temporal bone with cochlear midmodiolar axis view.

Figure 11A:
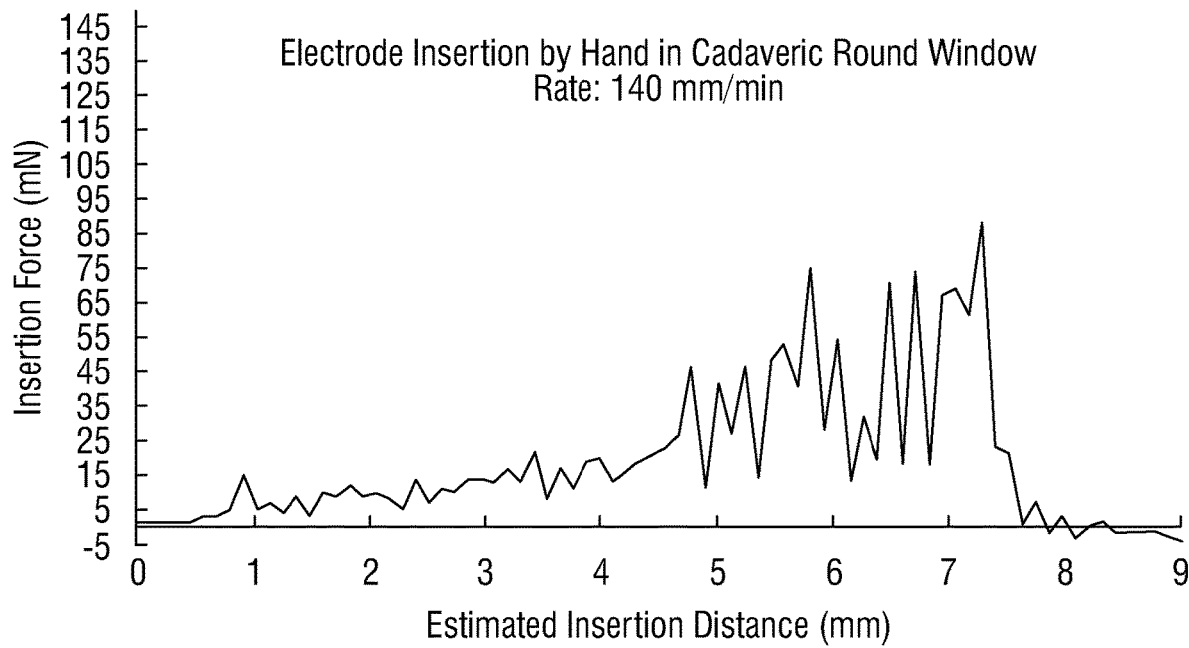
FIG. 11a is a graph illustrating an insertion force profile by hand in a Cadaveric cochlea through the round window as a function of cochlea insertion depth.
Figure 11B:
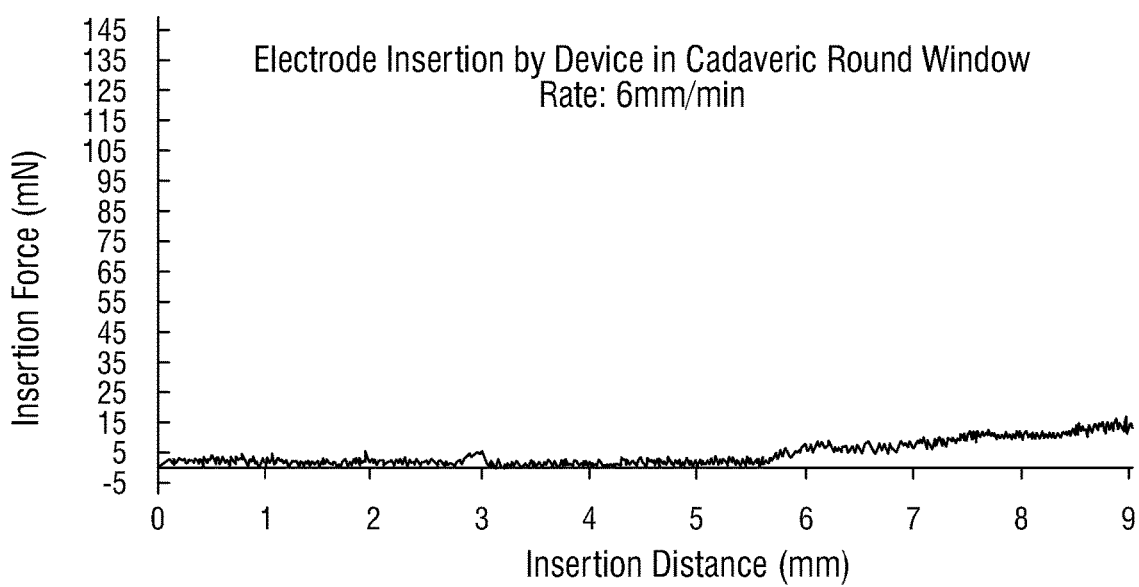
FIG. 11b is a graph illustrating an insertion force profile by the present disclosure in a Cadaveric cochlea through the round window as a function of cochlea insertion depth.

Compared to standard manual surgical insertion forces, the preliminary results showed a 7× decrease in maximum insertion force and a decrease in insertion force variability using the present control system components (FIGS. 11a and 11b). Through a controlled insertion protocol, the maximum insertion force using components of the system were 20.1±4.9 mN (Table 2), which is less than about 30-40 mN force required to damage the basilar membrane, a vital and delicate intracochlear structure important for preservation of hearing.

TABLE 2

Manual versus the present motorized (benchtop model) insertion forces

|  | Electrode Insertion by Hand into Cadaveric Cochlea through the Round Window | Electrode Insertion by Device into Cadaveric cochlea through the Round Window |
| --- | --- | --- |
| Average Max Insertion Force (mN) | 144.2 ± 31.5 | 20.1 ± 4.9 |
| Average Insertion Rate (um/sec) | 2018 ± 424 | constant 100 |
| (mm/min) | 121 ± 25 | constant 6 |
| Insertion Force Standard Deviation (mN) | 28.4 | 4.49 |

A novel device for post-operative adjustment of a neural stimulator has been described. Different arrangements of driving surfaces and mechanisms for coupling the electrode to the motor can be made and still be within the spirit of the invention.

It should be understood that the foregoing description relates to exemplary embodiments of the invention and that modifications may be made without departing from the spirit and scope of the invention as set forth in the following claims.

The claims appended hereto should be taken as the sole representation of the breadth of the present disclosure and the corresponding scope of the various embodiments described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It is also noted that recitations herein of "at least one" component, element, etc., should not be used to create an inference that the alternative use of the articles "a" or "an" should be limited to a single component, element, etc.

It is further noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

In this disclosure, it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

While the invention has been described with respect to a limited number of embodiments, those skilled in the art, having benefit of this disclosure, will appreciate that other embodiments can be devised that do not depart from the scope of the invention as disclosed herein. Accordingly, the scope of the invention should be limited only by the attached claims.

The invention claimed is:

1. An implantable system for post-surgical movement of an electrode within a patient's body, comprising:
   a hermetically sealed main body adapted for implantation into the patient's body;
   a drive wheel comprising a drive surface;
   an elongate member carrying the electrode;
   a motor mounted inside the hermetically sealed main body, the motor coupleable to the electrode via the drive wheel and remotely operable to move the electrode relative to the main body, wherein the drive surface of the drive wheel is configured to frictionally engage the elongate member carrying the electrode to move the electrode; and
   a position sensor sensing the position of the electrode.

2. The implantable system of claim 1, further comprising a hollow sheath having a proximal end and a distal end, wherein the proximal end of the hollow sheath is secured to a sheath anchor element of the hermetically sealed main body.

3. The implantable system of claim 2, wherein the hollow sheath further has a sealable tip at a terminal end of the distal end of the hollow sheath, wherein the sealable tip has a slit at an outer surface of the sealable tip.

4. The implantable system of claim 2, wherein the hollow sheath has a taper from the proximal end to the distal end.

5. The implantable system of claim 2, wherein the hollow sheath is sized to house the electrode.

6. The implantable system of claim 2, wherein the interior space of said hollow sheath is isolated from fluid communication with any portion of the hermetically sealed main body by extending said sheath through the hermetically sealed main body such that all spaces occupied by said electrode in the hermetically sealed main body are isolated from fluid communication with spaces housing said motor.

7. The implantable system of claim 1, wherein the motor is a piezoelectric motor.

8. The implantable system of claim 1, wherein the electrode is coupled to a speech processor.

9. The implantable system of claim 1, wherein the hermetically sealed main body stores a portion of the electrode.

10. The implantable system of claim 1, wherein the hermetically sealed main body further comprises an energy source configured to be charged wirelessly.

11. The implantable system of claim 1, wherein the hermetically sealed main body further comprises a circuit board.

12. The implantable system of claim 1, further comprising a wireless controller configured to control said motor.

13. The implantable system of claim 12, wherein the wireless controller charges an energy source within the hermetically sealed main body wirelessly.

14. The implantable system of claim 1, wherein the elongate member is a guide wire configured to push said electrode.

15. The implantable system of claim 1, wherein the position sensor is configured to connect to a pulley wheel with textured surface.

16. The implantable system of claim 1, further comprising a pulley wheel positioned adjacent the drive wheel to pinch the elongate member against the drive surface to enable movement of the electrode.

17. An implantable system for post-surgical manipulation of an electrode within a patient's body, the system comprising:
   a hollow sheath having a proximal end and a distal end, wherein the hollow sheath is configured to house the electrode;
   a drive assembly comprising:
      an implantable main body, wherein the main body has a sheath anchor element connected to the proximal end of the hollow sheath;
      a motor inside the implantable main body, wherein the motor is coupled to a controller adapted to receive wireless commands to drive the motor to manipulate the electrode inside the hollow sheath to enable post-surgical adjustment of the electrode position; and
      a drive wheel driven by the motor and configured to frictionally engage the electrode to move the electrode; and
   a position sensor sensing the position of the electrode.

18. The implantable system of claim 17, wherein the motor is a piezoelectric motor or a step motor.

19. The implantable system of claim 17, further comprising a pulley wheel adjacent the drive wheel and positioned to pinch the electrode between the drive wheel and the pulley wheel to enable the controller to manipulate the electrode.

20. The implantable system of claim 17, wherein the implantable main body further comprises an energy source configured to be charged wirelessly by a charging source external to the patient's body.

21. The implantable system of claim 17, wherein the hollow sheath further has a sealable tip at a terminal end of the distal end of the hollow sheath, wherein the sealable tip has a slit in an outer surface of the sealable tip.

* * * * *